United States Patent
Asaki et al.

(10) Patent No.: US 7,494,997 B2
(45) Date of Patent: Feb. 24, 2009

(54) AMIDE DERIVATIVE

(75) Inventors: Tetsuo Asaki, Uji (JP); Taisuke Hamamoto, Matsubara (JP); Yukiteru Sugiyama, Yamashina-ku (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 99 days.

(21) Appl. No.: 10/519,722

(22) PCT Filed: Jun. 27, 2003

(86) PCT No.: PCT/JP03/08192

§ 371 (c)(1),
(2), (4) Date: Dec. 28, 2004

(87) PCT Pub. No.: WO2004/002963

PCT Pub. Date: Jan. 8, 2004

(65) Prior Publication Data

US 2006/0014742 A1  Jan. 19, 2006

(30) Foreign Application Priority Data

| Jun. 28, 2002 | (JP) | ............................. 2002-189269 |
| Oct. 18, 2002 | (JP) | ............................. 2002-305146 |
| Dec. 26, 2002 | (JP) | ............................. 2002-377937 |

(51) Int. Cl.
C07D 401/04 (2006.01)
C07D 401/14 (2006.01)
C07D 403/04 (2006.01)
C07D 403/14 (2006.01)
A61K 31/506 (2006.01)
A61K 31/53 (2006.01)
A61P 35/00 (2006.01)

(52) U.S. Cl. .................. 514/242; 514/272; 514/252.01; 514/252.1; 514/252.12; 514/336; 544/182; 544/238; 544/336; 544/356; 544/358; 546/268.1

(58) Field of Classification Search .................. 544/182, 544/238, 336, 356, 358; 514/242, 272, 252.01, 514/252.1, 252.12, 336; 546/268.1
See application file for complete search history.

(56) References Cited

U.S. PATENT DOCUMENTS 5,521,184 A * 5/1996 Zimmermann ......... 514/252.11

FOREIGN PATENT DOCUMENTS

| WO | PCT/EP98/04427 | 1/1999 |
| WO | WO 02/22597 A1 | 3/2002 |

* cited by examiner

*Primary Examiner*—Venkataraman Balasubramanian
(74) *Attorney, Agent, or Firm*—Albert L. Jacobs, Jr.; Gerard F. Diebner

(57) ABSTRACT

The present invention provides an amide derivative represented by the following general formula (1):

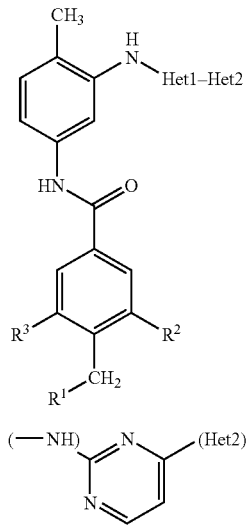

wherein $R^1$ represents a saturated cyclic amino group, $R^2$ represents alkyl, halogen or haloalkyl, $R^3$ represents hydrogen or halogen, Het 2 represents pyridyl or pyrimidinyl, and Het 1 represents a group of the formula [6], or a salt thereof, and a pharmaceutical composition comprising the same as an active ingredient.

The compound of the present invention is useful as a BCR-ABL tyrosine kinase inhibitor.

7 Claims, No Drawings

AMIDE DERIVATIVE

TECHNICAL FIELD

The present invention relates to an amide derivative or a salt thereof, and a pharmaceutical composition comprising an amide derivative or a salt thereof as an active ingredient.

While BCR-ABL tyrosine kinase (see, for example, Non-Patent Document 1) causes aberrant growth of cells, a compound which inhibits its activity is useful for the prevention or treatment of diseases caused by the activity of the BCR-ABL tyrosine kinase, for example, chronic myelogenous leukemia, acute lymphoblastic leukemia and acute myelogenous leukemia (see, for example, Non-Patent Document 2).

BACKGROUND ART bcr is gene which exists in the human twenty-second chromosome and abl is gene which exists in the human ninth chromosome, and Philadelphia chromosome is formed by translocation of the human twenty-second and ninth chromosomes. It is known that a gene product of the chromosome, BCR-ABL, is protein having tyrosine kinase activity and constantly generates the growth signal to cause aberrant growth of cells (see, for example, Non-Patent Document 2).

Therefore, inhibition of the BCR-ABL tyrosine kinase activity makes it possible to suppress cell growth caused by the kinase and a compound which inhibits the activity is suited for use as a therapeutic agent for diseases such as chronic myelogenous leukemia, acute lymphoblastic leukemia and acute myelogenous leukemia. Although Glivec® (see, for example, Patent Document 1) has already been put on the market as a drug having the same action, other drugs having the same action mechanism have never been put on the market and thus it has been required to develop more excellent medicines.

It has recently been reported that recurrence is often recognized in patients wherein remission is attained by administration of Glivec® in BCR-ABL-positive acute lymphoblastic leukemia, in addition to examples of blastic crisis of chronic myelogenous leukemia (see, for example, Non-Patent Document 3). As a result of examination of leukemia cells of the patients suffering from the recurrence of disease, the appearance of a variant such as E255K is recognized (see, for example, Non-Patent Documents 4 to 7). Also in examples of administration of Glivec® to the patients with BCR-ABL-positive acute lymphoblastic leukemia, the appearance of resistant cells which mainly exhibits variation of E255K is recognized (see, for example, Non-Patent Document 8). With an increase in use of Glivec®, resistant patients further increase and thus it is required to develop a therapy.

Patent Document 1:
  Japanese Unexamined Patent No. 6-87834

Patent Document 2:
  Pamphlet of International Publication WO 02/22597

Non-Patent Document 1:
  Shtivelman E, et al.: Nature, 1985, 315, 550-554

Non-Patent Document 2:
  Daley G Q, et al.: Science, 1990, 247, 824-830

Non-Patent Document 3:
  Druker B J, et al.: N Engl J Med, 2001, 344, 1038-1042

Non-Patent Document 4:
  Weisberg E, et al.: Drug Resist Updat, 2001, 4, 22-28

Non-Patent Document 5:
  Gorre M E, et al.: Science, 2001, 293, 876-880

Non-Patent Document 6:
  Blagosklonny M V: Leukemia, 2002, 16, 570-572

Non-Patent Document 7:
  Hochhaus A, et al.: Leukemia, 2002, 16, 2190-2196

Non-Patent Document 8:
  Hofmann W-K, et al.: blood, 2002, 99, 1860-1862

Non-Patent Document 9:
  Deninger W N, et al.: blood, 2000, 96, 3343-3356

Non-Patent Document 10:
  J. Org. Chem., 1996, 61, 1133-1135

Non-Patent Document 11:
  J. Org. Chem., 2000, 65, 1144-1157

Non-Patent Document 12:
  Recl. Trav. Chim. Pays-Bas., 1950, 69, 673-699

Non-Patent Document 13:
  J. Med. Chem., 2000, 43, 1508-1518

Non-Patent Document 14:
  J. Med. Chem., 1975, 18, 1077-1088

Non-Patent Document 15:
  Bioorg. Med. Chem. Lett., 2001, 11, 2235-2239

Non-Patent Document 16:
  J. Heterocyclic Chem., 2000, 37, 1457-1462

Non-Patent Document 17:
  J. Med. Chem., 2000, 43(8), 1508-1518

Non-Patent Document 18:
  Khim. Geterotsikl. Soedim., 1981, (7), 958-962

Non-Patent Document 19:
  J. Heterocyclic Chem., 1990, 27, 579-582

Non-Patent Document 20:
  Arzneim.-Forsch./Drug Res., 1989, 39(2), 1196-1201

Non-Patent Document 21:
  J. Org. Chem., 1996, 61, 7240-7241

DISCLOSURE OF THE INVENTION

An object of the present invention is to provide an amide derivative having an excellent BCR-ABL tyrosine kinase inhibitory activity, or a salt thereof.

The present inventors have intensively studied about various compounds and found that the above object is achieved by the amide derivative of the present invention, and thus the present invention has been completed.

That is, the present invention is directed to an amide derivative, which is a compound represented by the following formula [1] in any of the following cases (A) and (B), or a salt thereof (hereinafter referred to as a "compound of the present invention").

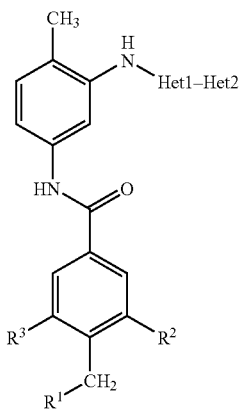

[1]

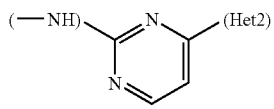

[6]

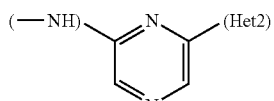

[7]

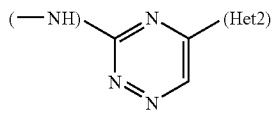

[8]

(A)

$R^1$ represents a saturated cyclic amino group (the saturated cyclic amino group may be substituted by 1 to 3 same or different members selected from the group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl), monoalkylamino or dialkylamino.

$R^2$ represents alkyl, halogen, haloalkyl, hydroxyalkyl, alkoxy, alkoxyalkyl, alkoxycarbonyl, acyl, amino, monoalkylamino, dialkylamino, nitro, carbamoyl, monoalkylcarbamoyl, dialkylcarbamoyl or cyano.

$R^3$ represents hydrogen, halogen or alkoxy.

Het1 represents any of groups of the following formulas [2] to [8].

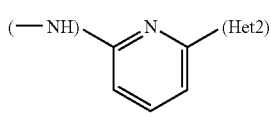

[2]

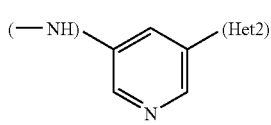

[3]

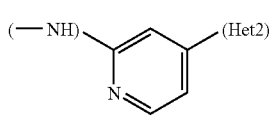

[4]

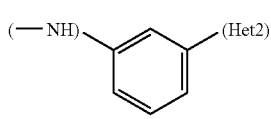

[5]

Het2 represents pyridyl, pyrimidinyl, pyrazinyl, pyridazinyl or 1,2-dihydropyridazinyl (the Het2 may be substituted by 1 to 3 same or different members selected from the group consisting of alkyl, halogen and amino).

Exception is made for a compound wherein $R^1$ is (i) pyrrolidinyl, piperidinyl, piperazinyl or morpholinyl, all of which may be substituted by 1 to 3 same or different members selected from the group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl, (ii) monoalkylamino, or (iii) dialkylamino, Het1 is a group of the formula [6], and Het2 is pyrazinyl or pyridyl which may be substituted by alkyl.

(B)

$R^1$ represents 4-methylpiperazin-1-yl, 1-pyrrolidinyl, piperidino, 4-ethylpiperazin-1-yl, 4-n-propylpiperazin-1-yl, cis-3,5-dimethylpiperazin-1-yl, morpholino, dimethylamino or diethylamino.

$R^2$ represents methyl, halogen, trifluoromethyl, methoxy, methoxycarbonyl, nitro, dimethylcarbamoyl or cyano.

$R^3$ represents hydrogen, bromo or methoxy.

Het1 represents a group of the formula [6].

Het2 represents 3-pyridyl.

The present invention is also directed to a pharmaceutical composition comprising the above amide derivative or salt thereof as an active ingredient and, more particularly, to a BCR-ABL tyrosine kinase inhibitor comprising the above amide derivative or salt thereof as an active ingredient. Specific therapeutic agent for diseases includes therapeutic agent for chronic myelogenous leukemia, therapeutic agent for acute lymphoblastic leukemia and therapeutic agent for acute myelogenous leukemia.

Examples of preferable ones among the above amide derivatives or salts thereof include the following amide derivative or a salt thereof.

An amide derivative of the general formula [1] wherein $R^1$ is a saturated cyclic amino group (the saturated cyclic amino group may be substituted by 1 to 3 same or different members selected from the group consisting of alkyl and alkoxycarbonyl), monoalkylamino or dialkylamino, $R^2$ is alky, halogen, haloalkyl, alkoxy, alkoxycarbonyl, nitro, dialkylcarbamoyl or cyano, $R^3$ is hydrogen, halogen or alkoxy, Het1 is any of groups of the formulas [2] to [8], and Het2 is pyridyl, pyrimidinyl, pyrazinyl, pyridazinyl or 1,2-dihydropyridazinyl (the Het2 may be substituted by 1 to 3 same or different halogen), or a salt thereof.

Examples of particularly preferable ones among the above amide derivatives include amide derivatives of the following (1) to (40), or salts thereof:

(1) 3-bromo-4-(4-methylpiperazin-1-ylmethyl)-N-{4-methyl-3-[4-(3-pyridyl)pyrimidin-2-ylamino]phenyl}benzamide (2) 3-iodo-4-(4-methylpiperazin-1-ylmethyl)-N-{4-methyl-3-[4-(3-pyridyl)pyrimidin-2-ylamino]phenyl}benzamide, (3) 3-chloro-4-(4-methylpiperazin-1-ylmethyl)-N-{4-methyl-3-[4-(3-pyridyl)pyrimidin-2-ylamino]phenyl}benzamide, (4) 3-fluoro-4-(4-methylpiperazin-1-ylmethyl)-N-{4-methyl-3-[4-(3-pyridyl)pyrimidin-2-ylamino]phenyl}benzamide, (5) 4-(4-methylpiperazin-1-ylmethyl)-3-trifluoromethyl-N-{4-methyl-3-[4-(3-pyridyl)pyrimidin-2-ylamino]phenyl}benzamide, (6) 4-(4-methylpiperazin-1-ylmethyl)-3-trifluoromethyl-N-{4-methyl-3-[4-(5-pyrimidinyl)pyrimidin-2-ylamino]phenyl}benzamide, (7) 3-bromo-4-(4-methylpiperazin-1-ylmethyl)-N-{4-methyl-3-[4-(2-pyrazinyl)pyrimidin-2-ylamino]phenyl}benzamide, (8) 3-bromo-4-(4-methylpiperazin-1-ylmethyl)-N-{3-[4-(6-chloropyridin-3-yl)pyrimidin-2-ylamino]-4-methylphenyl}benzamide, (9) 3-bromo-4-(4-methylpiperazin-1-ylmethyl)-N-{3-[4-(5-bromopyridin-3-yl)pyrimidin-2-ylamino]-4-methylphenyl}benzamide,

(10) 4-(4-methylpiperazin-1-ylmethyl)-3-trifluoromethyl-N-{3-[4-(5-bromopyridin-3-yl)pyrimidin-2-ylamino]-4-methylphenyl}benzamide,

(11) 3-bromo-4-(4-methylpiperazin-1-ylmethyl)-N-{3-[4-(1,2-dihydropyridazin-4-yl)pyrimidin-2-ylamino]-4-methylphenyl}benzamide,

(12) 3-bromo-4-(4-methylpiperazin-1-ylmethyl)-N-{4-methyl-3-[4-(3-pyridazinyl)pyrimidin-2-ylamino]phenyl}benzamide,

(13) 3-bromo-4-(4-methylpiperazin-1-ylmethyl)-N-{4-methyl-3-[4-(5-pyrimidinyl)pyrimidin-2-ylamino]phenyl}benzamide,

(14) 3-bromo-4-(4-methylpiperazin-1-ylmethyl)-N-{4-methyl-3-[4-(3-pyridyl)pyridin-2-ylamino]phenyl}benzamide,

(15) 3-bromo-4-(4-methylpiperazin-1-ylmethyl)-N-{4-methyl-3-[4-(5-pyrimidinyl)pyridin-2-ylamino]phenyl}benzamide,

(16) 3-bromo-4-(4-methylpiperazin-1-ylmethyl)-N-{4-methyl-3-[2-(3-pyridyl)pyridin-6-ylamino]phenyl}benzamide,

(17) 3-bromo-4-(4-methylpiperazin-1-ylmethyl)-N-{4-methyl-3-[3-(3-pyridyl)pyridin-5-ylamino]phenyl}benzamide,

(18) 3-bromo-4-(4-methylpiperazin-1-ylmethyl)-N-{4-methyl-3-[3-(3-pyridyl)phenylamino]phenyl}benzamide,

(19) 3-bromo-4-(4-methylpiperazin-1-ylmethyl)-N-{4-methyl-3-[2-(3-pyridyl)pyrazin-6-ylamino]phenyl}benzamide,

(20) 3-bromo-4-(4-methylpiperazin-1-ylmethyl)-N-{4-methyl-3-[5-(3-pyridyl)-1,2,4-triazin-3-ylamino]phenyl}benzamide,

(21) 3-methyl-4-(4-methylpiperazin-1-ylmethyl)-N-{4-methyl-3-[4-(3-pyridyl)pyrimidin-2-ylamino]phenyl}benzamide,

(22) 4-(4-methylpiperazin-1-ylmethyl)-3-nitro-N-{4-methyl-3-[4-(3-pyridyl)pyrimidin-2-ylamino]phenyl}benzamide,

(23) 3-methoxy-4-(4-methylpiperazin-1-ylmethyl)-N-{4-methyl-3-[4-(3-pyridyl)pyrimidin-2-ylamino]phenyl}benzamide,

(24) 3,5-dibromo-4-(4-methylpiperazin-1-ylmethyl)-N-{4-methyl-3-[4-(3-pyridyl)pyrimidin-2-ylamino]phenyl}benzamide,

(25) 3,5-dimethoxy-4-(4-methylpiperazin-1-ylmethyl)-N-{4-methyl-3-[4-(3-pyridyl)pyrimidin-2-ylamino]phenyl}benzamide,

(26) 3-(N,N-dimethylcarbamoyl)-4-(4-methylpiperazin-1-ylmethyl)-N-{4-methyl-3-[4-(3-pyridyl)pyrimidin-2-ylamino]phenyl}benzamide,

(27) 3-bromo-4-(4-ethylpiperazin-1-ylmethyl)-N-{4-methyl-3-[4-(3-pyridyl)pyrimidin-2-ylamino]phenyl}benzamide,

(28) 3-bromo-4-[4-(n-propyl)piperazin-1-ylmethyl]-N-{4-methyl-3-[4-(3-pyridyl)pyrimidin-2-ylamino]phenyl}benzamide,

(29) 3-bromo-4-(N,N-dimethylaminomethyl)-N-{4-methyl-3-[4-(3-pyridyl)pyrimidin-2-ylamino]phenyl}benzamide,

(30) 3-bromo-4-(N,N-diethylaminomethyl)-N-{4-methyl-3-[4-(3-pyridyl)pyrimidin-2-ylamino]phenyl}benzamide,

(31) 3-bromo-4-(1-pyrrolidinylmethyl)-N-{4-methyl-3-[4-(3-pyridyl)pyrimidin-2-ylamino]phenyl}benzamide,

(32) 3-bromo-4-(piperidinomethyl)-N-{4-methyl-3-[4-(3-pyridyl)pyrimidin-2-ylamino]phenyl}benzamide,

(33) 3-bromo-4-(morpholinomethyl)-N-{4-methyl-3-[4-(3-pyridyl)pyrimidin-2-ylamino]phenyl}benzamide,

(34) 3-bromo-4-(cis-3,5-dimethylpiperazin-1-ylmethyl)-N-{4-methyl-3-[4-(3-pyridyl)pyrimidin-2-ylamino]phenyl}benzamide,

(35) 3-bromo-4-(4-methyl-hexahydro-1H-1,4-diazepin-1-ylmethyl)-N-{4-methyl-3-[4-(3-pyridyl)pyrimidin-2-ylamino]phenyl}benzamide,

(36) 3-bromo-4-(1-piperazinylmethyl)-N-{4-methyl-3-[4-(5-pyrimidinyl)pyrimidin-2-ylamino]phenyl}benzamide,

(37) 4-[4-(t-butoxycarbonyl)piperazin-1-ylmethyl]-3-trifluoromethyl-N-{4-methyl-3-[4-(5-pyrimidinyl)pyrimidin-2-ylamino]phenyl}benzamide,

(38) 4-(1-piperazinylmethyl)-3-trifluoromethyl-N-{4-methyl-3-[4-(5-pyrimidinyl)pyrimidin-2-ylamino]phenyl}benzamide,

(39) 3-methoxycarbonyl-4-(4-methylpiperazin-1-ylmethyl)-N-{4-methyl-3-[4-(3-pyridyl)pyrimidin-2-ylamino]phenyl}benzamide, and

(40) 3-cyano-4-(4-methylpiperazin-1-ylmethyl)-N-{4-methyl-3-[4-(3-pyridyl)pyrimidin-2-ylamino]phenyl}benzamide.

The compound of the present invention has BCR-ABL tyrosine kinase inhibitory activity and is useful as a therapeutic agent for diseases such as chronic myelogenous leukemia, acute lymphoblastic leuke and acute myelogenous leukemia (see, for example, Non-Patent Document 9).

The compound of the above formula [1] in the case (B) is seemed to be described in prior art documents (see, for example, Patent Document 1 or 2), but is not specifically disclosed in the publication. Also the compound of the above formula [1] in the case (A) is not described in any documents.

The present invention will now be described in detail.

Examples of the "saturated cyclic amino group" include 4- to 8-membered saturated ring group which has a saturated ring group having at least one nitrogen atom as an atom composing the ring and also may have 1 to 3 same or different members selected from the group consisting of nitrogen atom, oxygen atom and sulfur atom. When the atom composing the ring of the cyclic amino is a nitrogen atom or a sulfur atom, the nitrogen atom or sulfur atom may form an oxide. Examples thereof include pyrrolidinyl, piperidinyl, piperazinyl, morpholinyl, thiomorpholinyl and hexahydro-1H-1,4-diazepinyl. These substituents may have a bonding hand at any position. Specifically, it means that "pyrrolidinyl" includes all of 1-pyrrolidinyl, 2-pyrrolidinyl and 3-pyrrolidinyl.

"Alkyl" includes straight or branched alkyl groups having 1 to 10 carbons, for example, methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl, n-nonyl and n-decyl. Straight alkyl groups having 1 to 3 carbon atoms are particularly preferred.

The alkyl moiety of "haloalkyl", "alkoxycarbonyl", "hydroxyalkyl", "monoalkylamino", "dialkylamino", "monoalkylcarbamoyl", "dialkylcarbamoyl", "alkoxy", "alkoxyalkyl" and "hydroxyalkyl" includes the above-mentioned alkyl.

"Halogen" includes, for example, fluorine, chlorine, bromine and iodine.

"Haloalkyl" includes monohaloalkyl, dihaloalkyl and trihaloalkyl, and the halogen moiety of "haloalkyl" includes the above-mentioned halogen. "Haloalkyl" includes, for example, trifluoromethyl and 2,2,2-trifluoroethyl.

"Acyl" includes acyl groups having 1 to 11 carbons, for example, formyl, acetyl, propionyl, butyryl, isobutyryl, benzoyl, 1-naphthoyl and 2-naphthoyl.

"Pyridyl" includes, for example, 2-pyridyl, 3-pyridyl and 4-pyridyl.

"Pyrimidinyl" includes, for example, 2-pyrimidinyl, 4-pyrimidinyl and 5-pyrimidinyl.

"Pyrazinyl" includes, for example, 2-pyrazinyl.

"Pyridazinyl" includes, for example, 3-pyridazinyl and 4-pyridazinyl.

"1,2-dihydropyridazinyl" includes, for example, 1,2-dihydropyridazin-3-yl and 1,2-dihydropyridazin-4-yl.

The compound of the present invention can be produced from per se known compound or an intermediate which can be produced with ease, for example, by the following method. In the production of the compound of the present invention, it is common that the raw materials are used for reaction after protecting with proper protecting groups by the per se known methods, when the raw materials have substituents intended not to be reacted. After the reaction, the protecting groups can be removed by per se known methods.

Process 1

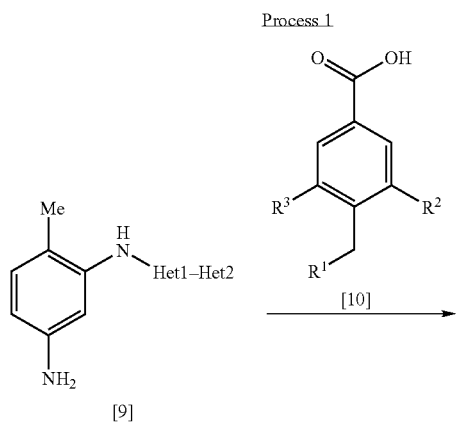

[9]

-continued

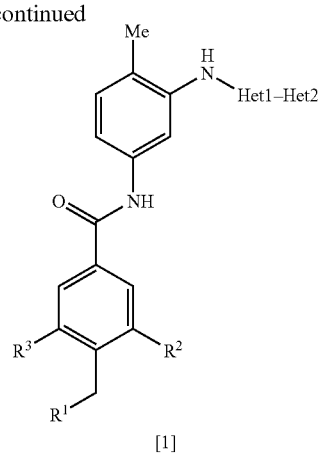

[1]

wherein $R^1$, $R^2$, $R^3$, Het1 and Het2 are as defined above.

This reaction is a condensation reaction of a compound [9] and a compound [10] and is therefore conducted by per se known methods used in the condensation reaction. A compound [1] can be produced by reacting a carboxylic acid as a compound [10] or a reactive derivative thereof with an amine as a compound [9]. Examples of the reactive derivative of the compound [10] include those which are usually used in the amide condensation formation reaction, for example, acid halide (e.g. acid chloride, acid bromide, etc.), mixed acid anhydride, imidazolide and active amide. When using the carboxylic acid [10], a condensing agent (e.g. 1,1'-oxalyldiimidazole, 1-ethyl-3-(3-dimethylaminopropyl)carbodiimide, dicyclohexylcarbodiimide, diethyl cyanophosphonate, diphenylphosphoryl azide, 2-chloro-1-methylpyridinium iodide, etc.) is used and the reaction is conducted at −20 to 100° C. in the presence or absence of a base (e.g. organic base such as triethylamine, N,N-diisopropyl-N-ethylamine, N,N-dimethylaniline, pyridine, 4-dimethylaminopyridine, 1,8-diazabicyclo[5.4.0]undec-7-ene, etc). The solvent is not specifically limited as far as it is not involved in the reaction and examples thereof include ethers such as tetrahydrofuran and diethyl ether; amides such as N,N-dimethylformamide and N,N-dimethylacetamide; nitriles such as acetonitrile and propionitrile; hydrocarbons such as benzene and toluene; halogenated hydrocarbons such as chloroform and dichloromethane; and solvent mixtures thereof. In that case, additives (e.g. 1-hydroxybenzotriazole, N-hydroxysuccinimide, etc.) can also be added. The reaction time varies depending on the kinds of the raw material and the condensing agent and the reaction temperature, but is preferably from 30 minutes to 24 hours. The amount of the compound [10] and the condensing agent is preferably 1 to 3 mol per mol of the compound [9]. When using an acid halide as the reactive derivative of the compound [10], the reaction is conducted at −20 to 100° C. using a pyridine solvent such as pyridine or 4-methylpyridine or the same base and solvent as those described above. Also 4-dimethylaminopyridine can be added as an additive. The reaction time varies depending on the kind of the acid halide and the reaction temperature, but is preferably from 30 minutes to 24 hours.

The compound [9] as the raw compound wherein Het1 is a group of the formula [6] can be prepared by the same manner as described in Patent Document 1.

The compound [9] as the raw compound wherein Het1 is a group of the formula [4], [5] or [7] can be prepared by the following manner:

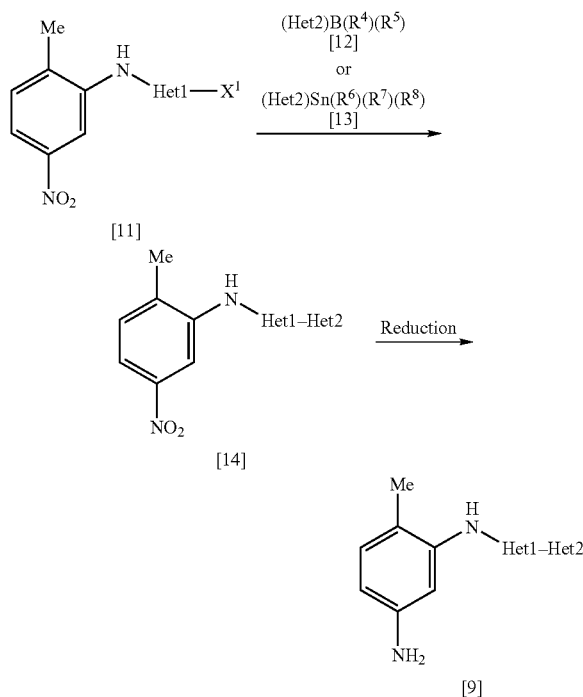

wherein Het1 and Het2 are as defined above, $R^4$ and $R^5$ represent alkyl or hydroxy, $R^6$, $R^7$ and $R^8$ represent alkyl, and $X^1$ represents halogen.

Step 1

This reaction is a cross-coupling reaction using a compound [11] and an organoboron compound [12] or an organotin compound [13] and can be conducted by per se known methods. For example, this reaction is conducted at 20 to 200° C. in a suitable solvent in the presence of a palladium catalyst. As the palladium catalyst, tetrakis(triphenylphosphine)palladium, dichlorobis(triphenylphosphine)palladium and dichlorobis(tri-o-tolylphosphine)palladium are usually used. The reaction solvent is not specifically limited as far as it is not involved in the reaction and examples thereof include ethers such as tetrahydrofuran, 1,4-dioxane and 1,2-dimethoxyethane; alcohols such as methanol and ethanol; amides such as N,N-dimethylformamide and N,N-dimethylacetamide; hydrocarbons such as benzene, toluene and xylene; organic amines such as pyridine and triethylamine; and solvent mixtures thereof. When using the compound [12], the addition of a base (e.g. sodium hydroxide, potassium carbonate, tripotassium phosphate, etc.) is essential. The reaction time varies depending on the kind of the raw material and the reaction temperature, but is preferably from 1 to 48 hours.

Step 2

This reaction is a reaction of reducing an aromatic nitro group of a compound [14] into an amino group and is therefore conducted by per se known methods used in the reducing reaction. The method includes, for example, a method of treating with zinc or tin under the acidic conditions. According to the catalytic reduction method, for example, hydrogenation can be conducted using platinum, Raney nickel, platinum-carbon (Pt—C), palladium-carbon (Pd—C) or ruthenium complex as the catalyst. In addition, a method of using a sulfide such as sodium dithionite and a method of reducing with ammonium formate or hydrazine in the presence of a metal catalyst are exemplified.

The compound [11] as the raw compound wherein Het1 is a group of the formula [4] can be prepared by reacting 2,4-dichloropyridine (prepared, for example, by version of the method described in Non-Patent Document 12) with 2-methyl-5-nitroaniline using the method of J. P. Wolfe et al. using a palladium catalyst (see Non-Patent Documents 10 and 11). When Het1 is a group of the formula [0.5], for example, the compound can be prepared by reacting 1-bromo-3-iodobenzene with 2-methyl-5-nitroaniline. When Het1 is a group of the formula [7], for example, the compound can be prepared by reacting 2,6-dichloropyrazine with 2-methyl-5-nitroaniline.

The reaction solvent is not specifically limited as far as it is not involved in the reaction and examples thereof include ethers such as tetrahydrofuran, 1,4-dioxane and 1,2-dimethoxyethane; hydrocarbons such as benzene, toluene and xylene; and solvent mixtures thereof. The reaction is conducted at 70 to 100° C. in the presence of a base. Examples of the palladium catalyst include tris(dibenzylideneacetone)dipalladium(0), palladium(II) acetate and tri(o-tolylphosphine)palladium(0). The amount of palladium is preferably from 0.5 to 4 mol % based on the halogenated aryl. As a ligand of the palladium catalyst, for example, 1,3-bis(diphenylphosphino)propane, 1,1'-bis(diphenylphosphino)ferrocene and (±)-2,2'-bis(diphenylphosphino)-1,1'-binaphthyl [(±)-BINAP] can be used. Examples of the base include sodium t-butoxide, potassium t-butoxide, cesium carbonate, potassium carbonate and sodium carbonate. The reaction time varies depending on the kind of the raw material and the reaction temperature, but is preferably from 1 to 36 hours.

The compound [11] wherein Het1 is a group of [4] can also be prepared by reacting 2,4-dichloropyridine with 2-methyl-5-nitroaniline at 20 to 200° C. in a suitable solvent in the presence or absence of a base. Examples of the base include pyridine, triethylamine, N,N-diisopropyl-N-ethylamine, potassium carbonate, sodium hydrogen carbonate and potassium hydroxide. The solvent is not specifically limited as far as it is not involved in the reaction and examples thereof include ethers such as tetrahydrofuran, dibutyl ether and 1,4-dioxane; amides such as N,N-dimethylformamide and N,N-dimethylacetamide; hydrocarbons such as benzene and toluene; alcohols such as ethylene glycol and 2-methoxyethanol; halogenated hydrocarbons such as chloroform and dichloromethane; dimethyl sulfoxide; and solvent mixtures thereof. The reaction time varies depending on the kind of the raw material and the reaction temperature, but is preferably from 1 to 24 hours.

The compound [14a] as the raw compound (compound [14] wherein Het1 is a group of the formula [4]) can also be prepared by the following manner:

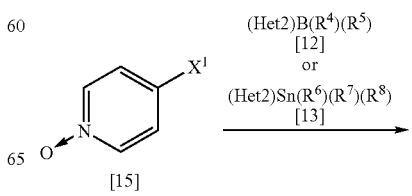

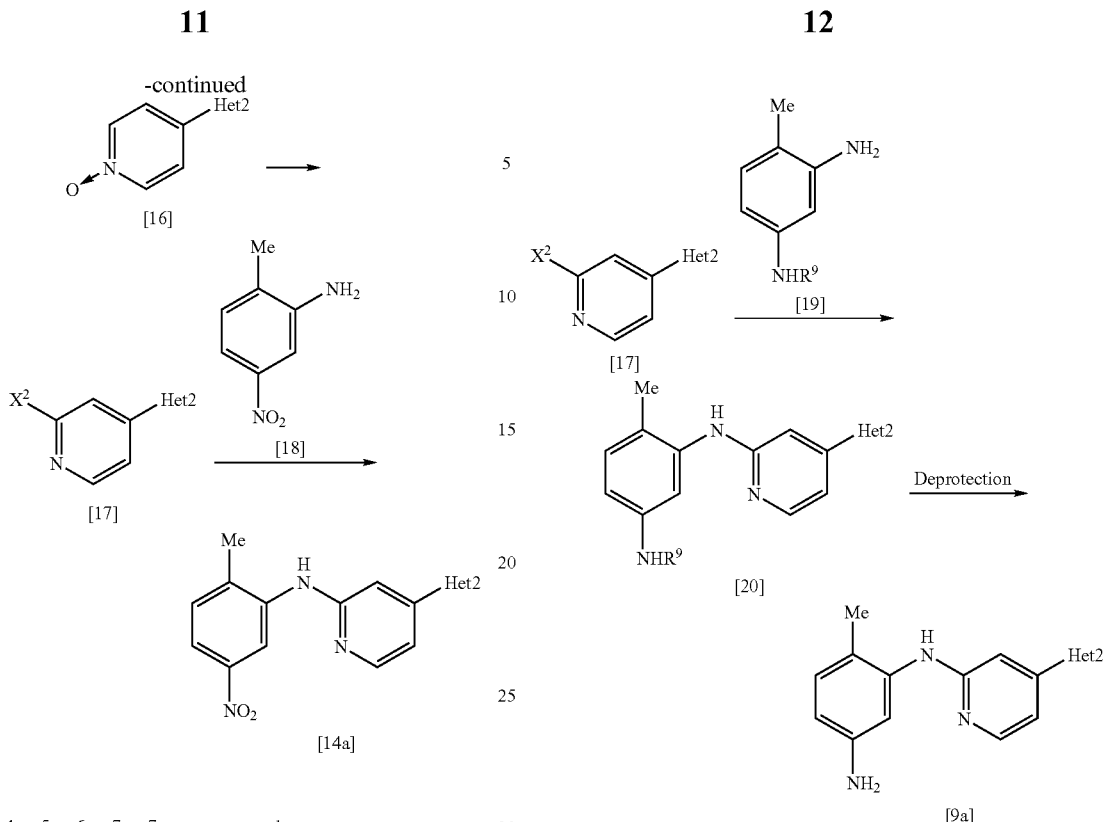

wherein $R^4$, $R^5$, $R^6$, $R^7$, $R^7$, Het2 and $X^1$ are as defined above, and $X^2$ represents halogen.

Step 1

This reaction is a cross-coupling reaction using a compound [15] and an organoboron compound [12] or an organotin compound [13] and can be conducted by the same manner as described above.

Step 2

A compound [17] is prepared by halogenating a compound [16]. Therefore, the reaction is conducted by per se known methods. The reaction is conducted using phosphorus oxychloride, phosphorus oxybromide, phosphorus pentachoride or phosphorus pentabromide with or without solvent. The reaction solvent is not specifically limited as far as it is not involved in the reaction and examples thereof include ethers such as tetrahydrofuran, dibutyl ether and 1,4-dioxane; amides such as N,N-dimethylformamide and N,N-dimethylacetamide; halogenated hydrocarbons such as chloroform and dichloromethane; and solvent mixtures thereof. The reaction is usually conducted at room temperature to 130° C. and the reaction time is preferably from 20 minutes to 24 hours.

Step 3

A compound [14a] can be prepared by reacting the compound [17] with a compound [18] using the above method using a palladium catalyst (see, for example, Non-Patent Documents 10 and 11).

A compound [9a] (compound [9] wherein Het1 is a group of the formula [4]) can be prepared by reacting the compound [17] with a compound [19] using the above method using a palladium catalyst (see, for example, Non-Patent Documents 10 and 11) to give a compound [20] and deprotecting the compound [20].

wherein Het2 and $X^2$ are as defined above, and $R^9$ represents a protecting group Step 1

The raw compound [19] can be prepared by protecting 2,4-diaminotoluene with a suitable protecting group using per se known methods. Examples of the protecting group include acyl derivatives such as benzoyl, acetyl and formyl; and urethane type derivatives such as benzyloxycarbonyl, t-butoxycarbonyl and 2,2,2-trichloroethoxycarbonyl. A compound [20] can be prepared by reacting the compound [17] with the compound [19] using the above palladium catalyst.

Step 2

In the deprotection reaction of the compound [20], an acyl type protecting group is removed by hydrolysis using acid or alkali, or removed with ammonia water or hydrazine. Examples of the acid used in the hydrolysis include inorganic acids such as hydrochloric acid and sulfuric acid, and examples of the base include inorganic bases such as sodium hydroxide and potassium hydroxide. Examples of the reaction solvent include alcohols such as methanol and ethanol; ethers such as tetrahydrofuran and 1,4-dioxane; water; and solvent mixtures thereof. The reaction temperature is from 0 to 100° C. and the reaction time is usually from several minutes to 24 hours. When the protecting group is a urethane type derivative, the protecting group can be removed by hydrogenation using a palladium catalyst, or removed with hydrochloric acid, trifluoroacetic acid, trimethylsilyl iodide or boron trifluoride, although depending on the kind of the protecting group.

The raw compound [9] wherein Het1 is a group of the formula [8] can be prepared by version of the method described in Reference Example 18 described hereinafter.

The compound [10] as the raw compound can be prepared by the following manner:

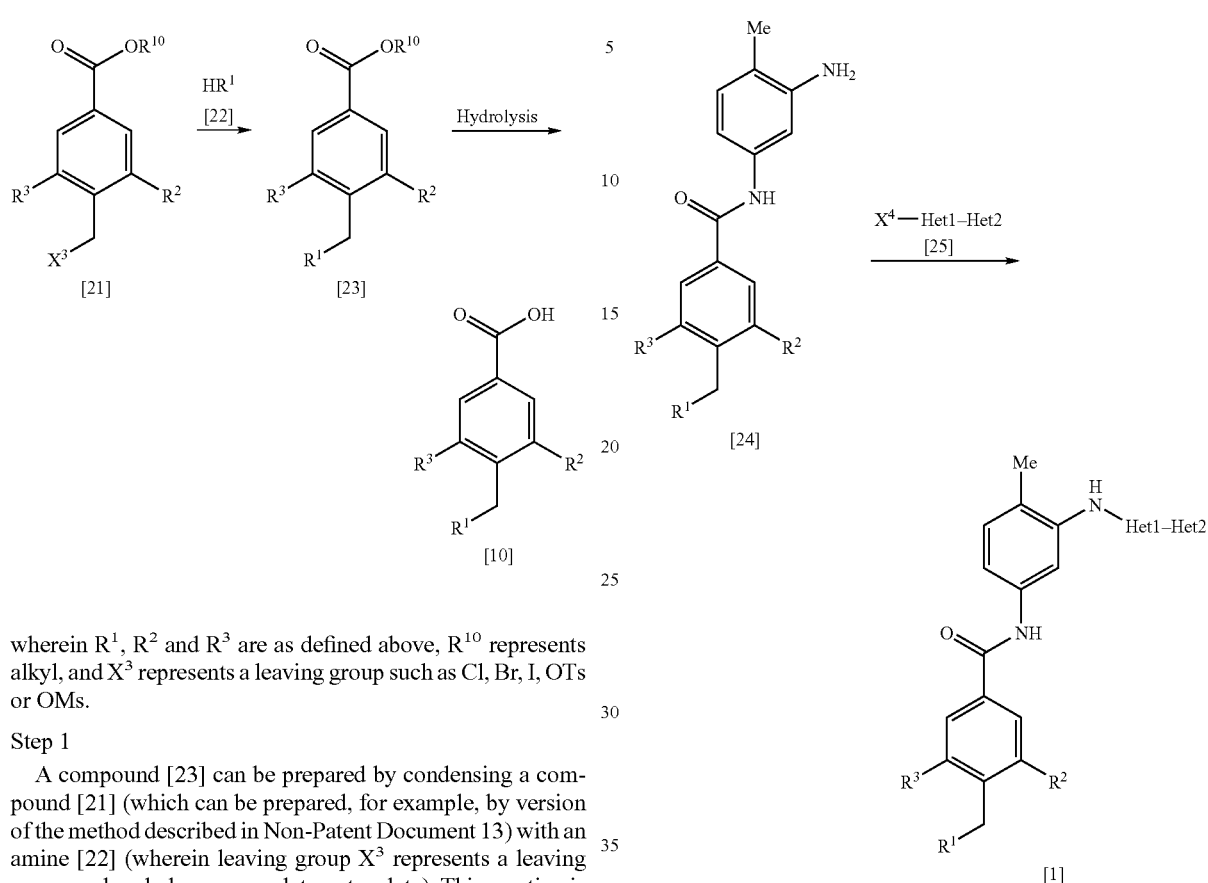

wherein $R^1$, $R^2$ and $R^3$ are as defined above, $R^{10}$ represents alkyl, and $X^3$ represents a leaving group such as Cl, Br, I, OTs or OMs.

Step 1

A compound [23] can be prepared by condensing a compound [21] (which can be prepared, for example, by version of the method described in Non-Patent Document 13) with an amine [22] (wherein leaving group $X^3$ represents a leaving group such as halogen, mesylate or tosylate). This reaction is a nucleophilic substitution reaction of an alkyl halide and amines and is conducted by per se known methods. This reaction is conducted in a suitable solvent using an excess amine or in the presence of a base. Examples of preferable base include pyridine, triethylamine, N,N-diisopropyl-N-ethylamine, potassium carbonate and sodium hydrogen carbonate. The solvent is not specifically limited as far as it is not involved in the reaction and examples thereof include ethers such as tetrahydrofuran and diethyl ether; amides such as N,N-dimethylformamide and N,N-dimethylacetamide; nitrites such as acetonitrile and propionitrile; hydrocarbons such as benzene and toluene; alcohols such as methanol and ethanol; water; and solvent mixtures thereof. The reaction temperature is usually from 0° C. to 100° C. The reaction time varies depending on the kind of the raw material and the reaction temperature, but is preferably from 30 minutes to 24 hours.

Step 2

A compound [10] can be prepared by hydrolyzing a compound [23]. The reaction is usually conducted in a suitable solvent in the presence of an acid or a base. Examples of the acid used in the hydrolysis include inorganic acids such as hydrochloric acid and sulfuric acid, and examples of the base include inorganic bases such as sodium hydroxide and potassium hydroxide. Examples of the reaction solvent include alcohols such as methanol and ethanol; ethers such as tetrahydrofuran and 1,4-dioxane; water; and solvent mixtures thereof. The reaction temperature is usually from 0 to 100° C. and the reaction time is usually from 30 minutes to 24 hours.

wherein $R^1$, $R^2$, $R^3$, Het1 and Het2 are as defined above, $X^4$ represents Cl, Br, I or $SR^{11}$, and $R^{11}$ represents alkyl A compound [1] can be prepared by reacting a compound [24] with a compound [25]. The reaction is conducted at 20 to 200° C. in a suitable solvent in the presence or absence of a base. Examples of the base include pyridine, triethylamine, N,N-diisopropyl-N-ethylamine, potassium carbonate, sodium hydrogen carbonate and potassium hydroxide. The solvent is not specifically limited as far as it is not involved in the reaction and examples thereof include ethers such as tetrahydrofuran, dibutyl ether and 1,4-dioxane; amides such as N,N-dimethylformamide and N,N-dimethylacetamide; hydrocarbons such as benzene and toluene; alcohols such as ethylene glycol and 2-methoxyethanol; halogenated hydrocarbons such as chloroform and dichloromethane; dimethyl sulfoxide; and solvent mixtures thereof. The reaction time varies depending on the kind of the raw material and the reaction temperature, but is preferably from 1 to 24 hours.

The compound [24] as the raw compound can be prepared by condensing 2,4-diaminotoluene with the compound [10] by version of the process 1.

The compound [25] as the raw compound can be prepared by using 2,6-dibromopyridine when Het1 is a group of the formula [2], 3,5-dibromopyridine when Het1 is a group of the formula [3], or 2,4-dichloropyrimidine when Het1 is a group of the formula [6] in accordance with the process 4 described hereinafter. When Het1 is a group of the formula [4], the compound [25] can also be prepared by the method described in the above-mentioned process 1.

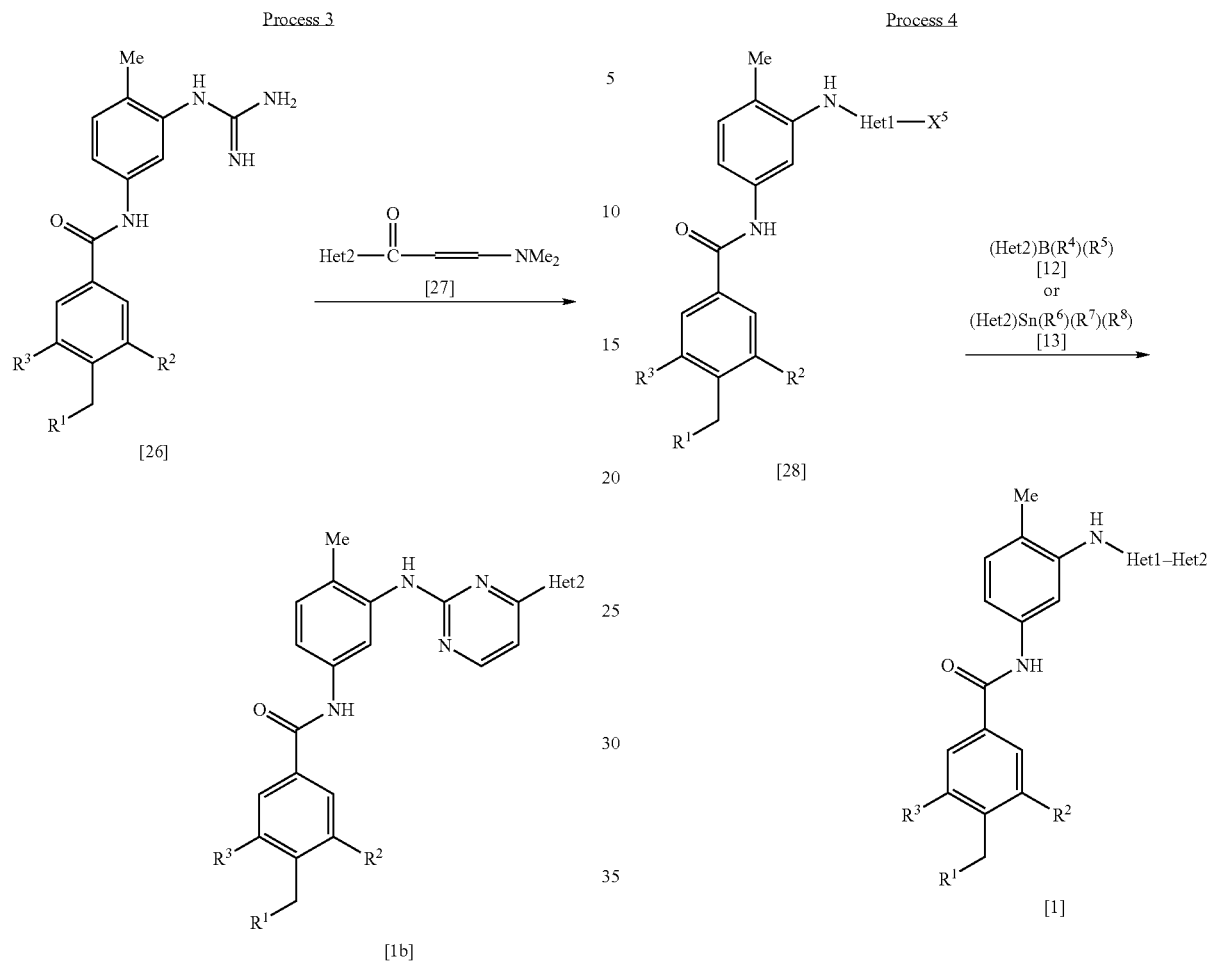

wherein $R^1$, $R^2$, $R^3$ and Het2 are as defined above A compound [1b] (compound [1] wherein Het1 is a group of the formula [6]) can be prepared by reacting a compound [26] or its acid addition salt with a compound [27]. The reaction is conducted at 20 to 200° C. in a suitable solvent. The solvent is not specifically limited as far as it is not involved in the reaction and examples thereof include alcohols such as methanol, ethanol, 2-propanol and 2-methoxyethanol. The amount of the compound [27] is from 1 to 2 mol, and preferably from 1 to 1.2 mol, per mol of the compound [26]. The reaction time varies depending on the kind of the raw material and the reaction temperature, but is preferably from 30 minutes to 30 hours. When using the acid addition salt of the compound [26], the reaction can be conducted by adding a suitable base (e.g. potassium carbonate, sodium hydrogen carbonate, sodium hydroxide, potassium hydroxide, etc).

The compound [26] as the raw compound can be prepared in the form of a free salt or an acid addition salt by reacting the compound [24] with cyanamide by the method described in the document (see, for example, Non-Patent Document 14).

The compound [27] as the raw compound can be prepared, for example, by version of the method described in Patent Document 1.

wherein $R^1$, $R^2R^3$, $R^4$, $R^5$, $R^6$, $R^7$, $R^8$, Het1 and Het2 are as defined above, and $X^5$ represents halogen This reaction is a cross-coupling reaction using a compound [28] and an organoboron compound [12] or an organotin compound [13] and can be conducted by per se known methods. For example, this reaction is conducted at 20 to 200° C. in a suitable solvent in the presence of a palladium catalyst. As the palladium catalyst, tetrakis(triphenylphosphine)palladium, dichlorobis(triphenylphosphine)palladium and dichlorobis(tri-o-tolylphosphine)palladium are used. The reaction solvent is not specifically limited as far as it is not involved in the reaction and examples thereof include ethers such as tetrahydrofuran, 1,4-dioxane and 1,2-dimethoxyethane; alcohols such as methanol and ethanol; amides such as N,N-dimethylformamide and N,N-dimethylacetamide; hydrocarbons such as benzene, toluene and xylene; organic amines such as pyridine and triethylamine; and solvent mixtures thereof. When using the compound [12], the addition of a base (e.g. sodium hydroxide, potassium carbonate, tripotassium phosphate, etc.) is essential. The reaction time varies depending on the kind of the raw material and the reaction temperature, but is preferably from 1 to 48 hours.

The compound [28] as the raw compound can be prepared by reacting a compound [24] with 4-hydroxy-2-(methylthio) pyridine when Het1 is a group of the formula [4], or reacting a compound [24] with 4-hydroxy-2-(methylthio)pyrimidine and treating the reaction product with phosphorus oxychloride (see, for example, Non-Patent Document 15) when Het1 is a group of the formula [6], or reacting by the method described in the document (see, for example, Non-Patent Document 16) using a compound [24] and 2,4-dichloropyrimidine when Het1 is a group of the formula [6].

The compound of the present invention can be used in the form of a free base as a medicine, however, it can be also used as a pharmaceutically acceptable salt made by the per se known methods. These salts include salts of mineral acids such as hydrochloric acid, hydrobromic acid, sulfuric acid and phosphoric acid, and salts of organic acids such as acetic acid, citric acid, tartaric acid, maleic acid, succinic acid, fumaric acid, p-toluene sulfonic acid, benzene sulfonic acid and methane sulfonic acid.

The hydrochloride of the amide derivative according to the present invention, for example, can be obtained by dissolving the amide derivative in an alcohol solution, an ethyl acetate solution or an ether solution of the hydrogen chloride.

As shown in test examples described hereinafter, the compound of the present invention has high inhibitory activity of BCR-ABL tyrosine kinase as compared with a pyrimidine derivative disclosed specifically in Patent Document 1. Therefore, the medicine of the present invention is useful as a preventive or therapeutic agent for diseases involved in BCR-ABL tyrosine kinase, for example, chronic myelogenous leukemia, acute lymphoblastic leukemia and acute myelogenous leukemia.

When the compound of the present invention is administered as a medicine, it can be administered to mammals, including humans, either by itself or as a pharmaceutical composition in which the compound is contained in a pharmaceutically acceptable non-toxic and inert carrier in the proportion of, for example, 0.1 to 99.5%, or preferably 0.5 to 90%.

One or more auxiliary agents for formulation such as fillers or a solid, semisolid or liquid diluent are used. It is desirable to administer the pharmaceutical composition in unit dosage form. The pharmaceutical composition of the present invention can be administered intravenously, orally, directly to the target tissue, topically (e.g., transdermally) or rectally. It is a matter of course that a dosage form suitable for any of the administration modes described above is employed. It is desirable to administer orally.

It is desirable to set the dosage of the compound as a BCR-ABL tyrosine kinase inhibitor or a therapeutic agent for chronic myelogenous leukemia by considering the condition of the patient, such as age, body weight, and the characteristics and severity of the disease and other factors such as the administration route; but usually for adults, an amount in the range of 0.1 to 1000 mg/person per day, and preferably 1 to 500 mg/person per day, is generally a dose of the compound of the present invention.

In some cases, amounts below this range are sufficient, and conversely, in other cases larger amounts are required. It can be administered by dividing the total dosage into two or three doses per day.

BEST MODE FOR CARRYING OUT THE INVENTION

The present invention will now described in more detail by way of Reference Examples, Examples, Test Examples and Formulation Examples of the compound of the present invention, to which, however, the present invention is not limited.

REFERENCE EXAMPLE 1

3-bromo-4-(4-methylpiperazin-1-ylmethyl)benzoyl chloride dihydrochloride

Step 1

Ethyl 3-bromo-4-methylbenzoate 10.00 g of 3-bromo-4-methylbenzoic acid was suspended in 100 ml of ethanol and 2.7 ml of concentrated sulfuric acid was added, and then the mixture was heated at reflux for 22 hours. After the solvent was distilled off under reduced pressure, the residue was mixed with iced water, neutralized with an aqueous saturated sodium hydrogen carbonate solution (pH8) and then extracted with ethyl acetate. The extract was washed with water and then dried over anhydrous magnesium sulfate. The solvent was distilled off under reduced pressure to obtain 10.99 g of the objective compound as a brown oily product.

$^1$H-NMR (CDCl$_3$) δ: 1.39 (3H, t), 2.45 (3H, s), 4.37 (2H, q), 7.29 (1H, dd), 7.87 (1H, dd), 8.20 (1H, d)

Step 2

Ethyl 3-bromo-4-(bromomethyl)benzoate

This compound was prepared by version of the method described in the document (J. Med. Chem., 2000, 43(8), 1508-1518). 10.00 g of ethyl 3-bromo-4-methylbenzoate obtained in the step 1 was dissolved in 125 ml of carbon tetrachloride and, after adding 6.83 g of N-bromosuccinimide and 80 g of benzoyl peroxide, the solution was heated at reflux under exposure to light from an incandescent lamp (1500 W) for 8 hours. After removing insolubles by filtration, the filtrate was diluted with 500 ml of dichloromethane. The solution was washed in turn with water and an aqueous saturated sodium hydrogen carbonate solution, and then dried over anhydrous magnesium sulfate. The solvent was distilled off under reduced pressure to obtain 13.02 g of a crude product as a brown oily product.

$^1$H-NMR (CDCl$_3$) δ: 1.40 (3H, t), 2.45 (3H, s), 4.37 (2H, q), 4.60 (2H, s), 7.52 (1H, d), 7.96 (1H, dd), 8.24 (1H, d)

Step 3

Ethyl 3-bromo-4-(4-methylpiperazin-1-ylmethyl)benzoate 11.40 g of ethyl 3-bromo-4-(bromomethyl)benzoate obtained in the step 2 was dissolved in 114 ml of anhydrous tetrahydrofuran and, after adding 5.3 g of potassium carbonate, 2.86 g of N-methylpiperazine in 10 ml of tetrahydrofuran solution was added dropwise over 10 minutes while stirring under an argon atmosphere at room temperature. After stirring at room temperature for 4 hours, insolubles were removed by filtration and the solvent in the filtrate was distilled off under reduced pressure. The residue was purified by silica gel column chromatography to obtain 7.53 g of the objective compound as a brown oily product.

$^1$H-NMR (CDCl$_3$) δ: 1.39 (3H, t), 2.30 (3H, s), 2.48 (4H, br), 2.57 (4H, br), 3.63 (2H, s), 4.38 (2H, q), 7.57 (1H, d), 7.94 (1H, dd), 8.20 (1H, d)

Step 4

3-bromo-4-(4-methylpiperazin-1-ylmethyl)benzoic acid dihydrochloride 2.00 g of ethyl 3-bromo-4-(4-methylpiperazin-1-ylmethyl)benzoate obtained in the step 3 was dissolved in 40 ml of methanol and, after adding 8.8 ml of an aqueous 1N sodium hydroxide solution, the mixture was heated at reflux for one hour. After the solvent was distilled off, the residue was dissolved in 40 ml of water. The solution was washed with 40 ml of ether and the aqueous layer was acidified (pH2) with 1N hydrochloric acid under ice cooling. After the water was distilled off, the operation of adding 50 ml of toluene to the residue followed by azeotropic removal of water was repeated three times to obtain 2.56 g of a crude product as a colorless crystal.

$^1$H-NMR ($D_2O$) δ: 3.04 (3H, s), 3.72 (8H, br), 4.66 (2H, s), 7.74 (1H, d), 8.05 (1H, d), 8.33 (1H, s)

Step 5

3-bromo-4-(4-methylpiperazin-1-ylmethyl)benzoyl chloride dihydrochloride 1.50 g of 3-bromo-4-(4-methylpiperazin-1-ylmethyl)benzoic acid dihydrochloride obtained in the step 4 was suspended in 6.3 ml of thionyl chloride, followed by stirring with heating for 24 hours. The reaction solution was air-cooled and the deposited crystal was collected by filtration and then washed with diethyl ether to obtain 1.34 g of a crude product as a colorless crystal.

Melting point: 229-231° C. (with decomposition)
$^1$H-NMR ($D_2O$) δ: 3.05 (3H, s), 3.83 (8H, br), 4.71 (2H, s), 7.76 (1H, d), 8.07 (1H, dd), 8.37 (1H, s)

REFERENCE EXAMPLE 2

3-iodo-4-(4-methylpiperazin-1-ylmethyl)benzoyl chloride dihydrochloride

In the same manner as in Reference Example 1, except that 3-iodo-4-methylbenzoic acid was used in place of 3-bromo-4-methylbenzoic acid in the step 1, a pale yellow crystal was prepared.

Melting point: 218-220° C. (with decomposition)
$^1$H-NMR ($D_2O$) δ: 3.09 (3H, s), 3.86 (8H, br), 4.71 (2H, s), 7.77 (1H, d), 8.13 (1H, dd), 8.66 (1H, d)

REFERENCE EXAMPLE 3

3-chloro-4-(4-methylpiperazin-1-ylmethyl)benzoyl chloride dihydrochloride

In the same manner as in Reference Example 1, except that 3-chloro-4-methylbenzoic acid was used in place of 3-bromo-4-methylbenzoic acid in the step 1, a colorless crystal was prepared.

Melting point: 245-247° C. (with decomposition)
$^1$H-NMR ($D_2O$) δ: 3.07 (3H, s), 3.84 (8H, br), 4.71 (2H, s), 7.79 (1H, d), 8.06 (1H, dd), 8.21 (1H, s)

REFERENCE EXAMPLE 4

3-fluoro-4-(4-methylpiperazin-1-ylmethyl)benzoyl chloride dihydrochloride

In the same manner as in Reference Example 1, except that 3-fluoro-4-methylbenzoic-acid was used in place of 3-bromo-4-methylbenzoic acid in the step 1, a colorless crystal was prepared.

Melting point: 242-244° C. (with decomposition)
$^1$H-NMR ($D_2O$) δ: 3.01 (3H, s), 3.63 (4H, br), 3.84 (4H, br), 4.63 (2H, s), 7.68 (1H, t), 7.89 (2H, t)

REFERENCE EXAMPLE 5

4-(4-methylpiperazin-1-ylmethyl)-3-trifluoromethyl-benzoyl chloride dihydrochloride In the same manner as in Reference Example 1, except that 4-methyl-3-trifluorobenzoic acid was used in place of 3-bromo-4-methylbenzoic acid in the step 1, a pale brown crystal was prepared.

Melting point: 214-216° C. (with decomposition)
$^1$H-NMR ($D_2O$) δ: 3.02 (3H, s), 3.81 (8H, br), 4.70 (2H, s), 7.91 (1H, d), 8.32 (1H, d), 8.44 (1H, s)

REFERENCE EXAMPLE 6

4-methyl-3-[4-(5-pyrimidinyl)pyrimidin-2-ylamino] aniline

Step 1

3-(dimethylamino)-1-(5-pyrimidinyl)-2-propen-1-one

This compound was prepared by version of the method described in the document (Japanese Unexamined Patent Publication (Kokai) No. 6-87834). 6.01 g of N,N-dimethylformamide dimethylacetal was added to 1.54 g of 5-acetylpyrimidine (Khim. Geterotsikl. Soedim., 1981, (7), 958-962) and the mixture was heated at reflux for 15 hours. After the reaction solution was air-cooled, a small amount of diisopropyl ether was added and the deposited crystal was collected by filtration to obtain 1.52 g of the objective compound as a reddish brown crystal.

Melting point: 133-135° C. $^1$H-NMR ($CDCl_3$) δ: 2.98 (3H, s), 3.22 (3H, s), 5.62 (1H, d), 7.89 (1H, d), 9.17 (2H, s), 9.27 (1H, s)

Step 2

1-(2-methyl-5-nitrophenyl)guanidine

To 135 g of 1-(2-methyl-5-nitrophenyl)guanidine nitrate (Japanese Unexamined Patent Publication (Kokai) No. 6-87834), 21 g of sodium hydroxide in 1.0 L of a cold aqueous solution was directly added, followed by stirring at room temperature for 10 minutes. The crystal was filtered, sufficiently washed with water and then forced-air dried at 60° C. to obtain 102 g of the objective compound as a pale yellow crystal.

Melting point: 135-142° C. $^1$H-NMR (DMSO-$d_6$) δ: 2.16 (3H, s), 5.31 (4H, br), 7.31 (1H, d), 7.48 (1H, d), 7.59 (1H, dd)

Step 3

1-methyl-4-nitro-2-[4-(5-pyrimidinyl)pyrimidin-2-ylamino] benzene

To 1.51 g of 3-(dimethylamino)-1-(5-pyrimidinyl)-2-propen-1-one obtained in the step 1, 1.66 g of 1-(2-methyl-5-nitrophenyl)guanidine obtained in the step 2 was added, followed by stirring at 120° C. for 2 hours. To the solidified reaction solution, 2-propanol was added and the crystal was collected by filtration and then washed in turn with 2-propanol and diethyl ether to obtain 1.95 g of the objective compound as a pale brown crystal.

Melting point: 200-203° C. $^1$H-NMR (DMSO-$d_6$) δ: 2.43 (3H, s), 7.53 (1H, d), 7.65 (1H, d), 7.91 (1H dd), 8.68 (1H, d), 8.77 (1H, d), 9.33 (2H, s), 9.47 (2H, s)

Step 4

4-methyl-3-[4-(5-pyrimidinyl)pyrimidin-2-ylamino]aniline

This compound was prepared by version of the method described in the document (Japanese Unexamined Patent Publication (Kokai) No. 6-87834). 1.95 g of 1-methyl-4-nitro-2-[4-(5-pyrimidinyl)pyrimidin-2-ylamino]benzene obtained in the step 3 was suspended in 300 ml of methanol and, after adding 0.50 g of 10% palladium-carbon, the mixture was hydrogenated at 30° C. under 4 atm for 18 hours. The catalyst was removed by filtration and the solvent in the filtrate was distilled off under reduced pressure. The residue was purified by silica gel column chromatography to obtain 0.60 g of the objective compound as a yellow amorphous.

$^1$H-NMR (CDCl$_3$) δ: 2.25 (3H, s), 3.64 (2H, br), 6.43 (1H, d), 6.99 (1H, s), 7.01 (1H, d), 7.14 (1H, dd), 7.52 (1H, s), 8.54 (1H, dd), 9.32 (1H, s), 9.35 (2H, s)

REFERENCE EXAMPLE 7

4-methyl-3-[4-(2-pyrazinyl)pyrimidin-2-ylamino]aniline

Step 1

3-(dimethylamino)-1-(2-pyrazinyl)-2-propen-1-one

This compound was prepared by version of the method described in the document (Japanese Unexamined Patent Publication (Kokai) No. 6-87834). To 5.00 g of 2-acetylpyrazine, 5.37 g of N,N-dimethylformamide dimethyl acetal was added and the mixture was heated at reflux for 19 hours. The reaction solution was air-cooled and the deposited crystal was dissolved in ethyl acetate and then concentrated under reduced pressure. After adding a small amount of diethyl ether, the deposited crystal was collected by filtration and then washed in turn with diethyl ether and diisopropyl ether to obtain 5.20 g of the objective compound as a brown crystal.

$^1$H-NMR (CDCl$_3$) δ: 3.01 (3H, s), 3.21 (3H, s), 6.36 (1H, d), 7.95 (1H, d), 8.61 (2H, m), 9.33 (1H, s)

Step 2

1-methyl-4-nitro-2-[4-(2-pyrazinyl)pyrimidin-2-ylamino]benzene

This compound was prepared by version of the method described in the document (Japanese Unexamined Patent Publication (Kokai) No. 0.6-87834). 2.00 g of 3-(dimethylamino)-1-(2-pyrazinyl)-2-propen-1-one obtained in the step 1 and 2.90 g of 1-(2-methyl-5-nitrophenyl)guanidine nitrate (Japanese Unexamined Patent Publication (Kokai) No. 6-87834) were suspended in 23 ml of 2-propanol and, after adding 0.50 g of sodium hydroxide, the mixture was heated at reflux for 20 hours. After air cooling the reaction solution, the deposited crystal was collected by filtration to obtain 3.25 g of a crude crystal. The crude crystal was dissolved in chloroform-methanol (2:1) and insolubles were removed by filtration, and then the filtrate was concentrated under reduced pressure to obtain 1.93 g of the objective compound as an ocherous crystal.

Melting point: 207-210° C. $^1$H-NMR (DMSO-d$_6$) δ: 2.44 (3H, s), 7.53 (1H, d), 7.74 (1H, d), 7.91 (1H, dd), 8.71 (1H, d), 8.81 (3H, m), 9.34 (1H, s), 9.47 (1H, s)

Step 3

4-methyl-3-[4-(2-pyrazinyl)pyrimidin-2-ylamino]aniline

This compound was prepared by version of the method described in the document (Japanese Unexamined Patent Publication (Kokai) No. 6-87834). 1.00 g of 1-methyl-4-nitro-2-[4-(2-pyrazinyl)pyrimidin-2-ylamino]benzene obtained in the step 2 was suspended in 50 ml of methanol and, after adding 100 mg of 10% palladium-carbon, the mixture was hydrogenated at room temperature under 3 atm for 14 hours and then hydrogenated under 3.4 atm for 4 hours. The catalyst was removed by filtration and the solvent in the filtrate was distilled off under reduced pressure. The residue was purified by silica gel column chromatography to obtain 0.49 g of the objective compound as a yellow amorphous.

$^1$H-NMR (CDCl$_3$) δ: 2.27 (3H, s), 3.69 (2H, br), 6.43 (1H, dd), 7.00 (1H, s), 7.02 (1H, d), 7.60 (1H, d), 7.70 (1H, d), 8.58 (1H, d), 8.67 (2H, m), 9.60 (1H, s)

REFERENCE EXAMPLE 8

3-[4-(6-chloropyridin-3-yl)pyrimidin-2-ylamino]-4-methylaniline

Step 1

5-acetyl-2-chloropyridine 1.84 g of ground magnesium chloride was suspended in 20 ml of toluene and 9.4 ml of triethylamine and 4.46 g of diethyl malonate were added in turn. After stirring at room temperature for 1.5 hours, 4.84 g of 6-chloronicotinoyl chloride in 10 ml of a toluene suspension was added dropwise over 20 minutes, followed by stirring at room temperature for 2 hours. After neutralizing with 60 ml of 1N hydrochloric acid, the aqueous layer was separated. The aqueous layer was further extracted with diethyl ether and the organic layers were combined, and then the solvent was distilled off under reduced pressure. To the resulting crude crystal, dimethyl sulfoxide-water (25 ml-1 ml) was added, followed by stirring with heating at 150 to 160° C. for 2 hours. The reaction solution was air-cooled and water was added, and then the deposited crystal was collected by filtration. The deposited crystal was dissolved in ethyl acetate and the solution was washed in turn with water and aqueous saturated sodium hydrogen carbonate solution and then dried over anhydrous magnesium sulfate. The resulting crude crystal was washed with diisopropyl ether and then collected by filtration to obtain 2.74 g of the objective compound as a semitranslucent crystal.

Melting point: 101-102° C. $^1$H-NMR (CDCl$_3$) δ: 2.64 (3H, d), 7.45 (1H, d), 8.20 (1H, dt), 8.94 (1H, d)

Step 2

1-(6-chloropyridin-3-yl)-3-(dimethylamino)-2-propen-1-one

This compound was prepared by version of the method described in the document (Japanese Unexamined Patent Publication (Kokai) No. 6-87834). To 2.68 g of 5-acetyl-2-chloropyridine obtained in the step 1, 2.26 g of N,N-dimethylformamide dimethyl acetal was added and the mixture was heated at reflux for 12 hours. After air cooling, the reaction solution was directly purified by silica gel column chromatography. The resulting crude crystal was washed with diethyl ether and then collected by filtration to obtain 1.87 g of the objective compound as a yellow crystal.

Melting point: 122-123° C. $^1$H-NMR (CDCl$_3$) δ: 2.96 (3H, s), 3.19 (3H, s), 5.62 (1H, d), 7.37 (1H, d), 7.85 (1H, d), 8.16 (1H, dd), 8.85 (1H, d)

Step 3

2-[4-(6-chloropyridin-3-yl)pyrimidin-2-ylamino]-1-methyl-4-nitrobenzene

To 1.83 g of 1-(6-chloropyridin-3-yl)-3-(dimethylamino)-2-propen-1-one obtained in the step 2 and 1.69 g of 1-(2- methyl-5-nitrophenyl)guanidine obtained in the step 2 of Reference Example 6, 18 ml of 2-propanol was added and the mixture was heated at reflux for 16 hours. After the reaction solution was air-cooled, the deposited crystal was collected by filtration and washed with diethyl ether. The resulting crude crystal was purified by silica gel column chromatography to obtain 0.91 g of the objective compound as a pale yellow crystal.

Melting point: 210-212° C. $^1$H-NMR (DMSO-$d_6$) δ: 2.42 (3H, s), 7.52 (1H, d), 7.59 (1H, d), 7.70 (1H, d), 7.90 (1H, dd), 8.53 (1H, dd), 8.64 (1H, d), 8.75 (1H, d), 9.15 (1H, d), 9.29 (1H, s)

Step 4

3-[4-(6-chloropyridin-3-yl)pyrimidin-2-ylamino]-4-methylaniline

To 842 mg of 2-[4-(6-chloropyridin-3-yl)pyrimidin-2-ylamino]-1-methyl-4-nitrobenzene obtained in the step 3, 6 ml of concentrated hydrochloric acid was added and a solution of 2.78 g of tin chloride(II) dihydrate in 4 ml of concentrated hydrochloric acid was added while stirring with heating at 55° C. The mixture was gradually heated up to 100° C. and further stirred with heating at 100° C. for 15 minutes. The reaction solution was air-cooled and water was added, and then alkalified with an aqueous 10% sodium hydroxide solution. After the addition of chloroform and stirring for a while, insolubles were removed by filtration and the aqueous layer was separated. The aqueous layer was further extracted with chloroform and the organic layers were combined and, after drying over anhydrous magnesium sulfate, the solvent was distilled off under reduced pressure. The residue was purified by silica gel column chromatography to obtain a crude product. The crude product was crystallized by adding diethyl ether and the crystal was collected by filtration to obtain 680 mg of the objective compound as a pale yellow crystal.

Melting point: 117-118° C. $^1$H-NMR (CDCl$_3$) δ: 2.25 (3H, s), 3.63 (2H, br), 6.42 (1H, dd), 6.95 (1H, s), 7.00 (1H, d), 7.10 (1H, d), 7.45 (1H, d), 7.54 (1H, s), 8.31 (1H, dd), 8.50 (1H, d), 9.03 (1H, d)

REFERENCE EXAMPLE 9

3-[4-(5-bromopyridin-3-yl)pyrimidin-2-ylamino]-4-methylaniline

Step 1

5-bromonicotinoyl chloride

To 5.00 g of 5-bromonicotinic acid, 74 ml of thionyl chloride was added and the mixture was heated at reflux for 6 hours. After the solvent was distilled off under reduced pressure, the crystal was washed with diisopropyl ether and collected by filtration to obtain 4.09 g of the objective compound as a colorless crystal.

Melting point: 72-74° C. $^1$H-NMR (CDCl$_3$) δ: 8.51 (1H, t), 8.96 (1H, d), 9.21 (1H, d)

Step 2

3-acetyl-5-bromopyridine 1.24 g of ground magnesium chloride was suspended in 13 ml of toluene and 6.2 ml of triethylamine and 2.93 g of diethyl malonate were added in turn. After stirring at room temperature for 1.5 hours, a suspension of 4.08 g of 5-bromonicotinoyl chloride obtained in the step 1 in 10 ml of toluene was added dropwise over 15 minutes, followed by stirring at room temperature for 2 hours. After neutralizing with 40 ml of 1N hydrochloric acid, the aqueous layer was separated. The aqueous layer was extracted with diethyl ether and the organic layers were combined, and then the solvent was distilled off under reduced pressure. To the resulting oily product, dimethyl sulfoxide-water (17 ml-0.7 ml) was added, followed by stirring with heating at 150 to 160° C. for 2 hours. The reaction solution was air-cooled and water was added, and then the deposited crystal was collected by filtration. The deposited crystal was dissolved in ethyl acetate, washed in turn with water and aqueous saturated sodium hydrogen carbonate solution and then dried over anhydrous magnesium sulfate. 0.60 g of activated carbon (Kyoryoku Shirasagi MOIWY433) was added and, after standing for 10 minutes, activated carbon was removed by filtration, the filtrate was concentrated under reduced pressure. The residue was purified by silica gel column chromatography to obtain 0.89 g of the objective compound as a pale yellow crystal.

Melting point: 87-89.5° C. $^1$H-NMR (CDCl$_3$) δ: 2.65 (3H, s), 8.37 (1H, t), 8.86 (1H, d), 9.07 (1H, d)

Step 3

1-(5-bromopyridin-3-yl)-3-(dimethylamino)-2-propen-1-one

This compound was prepared by version of the method described in the document (Japanese Unexamined Patent Publication (Kokai) No. 6-87834). To 859 mg of 3-acetyl-5-bromopyridine obtained in the step 2, 563 mg of N,N-dimethylformamide dimethyl acetal was added and the mixture was heated at reflux for one hour. After air cooling, the reaction solution was directly purified by silica gel column chromatography. The resulting crude crystal was washed with diethyl ether and then collected by filtration to obtain 860 mg of the objective compound as a yellow crystal.

Melting point: 131-131.5° C. $^1$H-NMR (CDCl$_3$) δ: 2.98 (3H, s), 3.21 (3H, s), 5.63 (1H, d), 7.87 (1H, d), 8.33 (1H, t), 8.73 (1H, d), 8.98 (1H, d)

Step 4

2-[4-(5-bromopyridin-3-yl)pyrimidin-2-ylamino]-1-methyl-4-nitrobenzene

To 833 mg of 1-(5-bromopyridin-3-yl)-3-(dimethylamino)-2-propen-1-one obtained in the step 3 and 634 mg of 1-(2-methyl-5-nitrophenyl)guanidine obtained in the step 2 of Reference Example 6, 7 ml of 2-propanol was added and the mixture was heated at reflux for 17 hours. After the reaction solution was air-dried, the deposited crystal was collected by filtration and washed with diethyl ether to obtain 823 mg of the objective compound as a pale yellow crystal.

Melting point: 206-208° C. $^1$H-NMR (DMSO-$d_6$) δ: 2.43 (3H, s), 7.52 (1H, d), 7.66 (1H, d), 7.90 (1H, dd), 8.66 (1H, d), 8.74 (1H, d), 8.80 (1H, d), 8.86 (1H, d), 9.31 (2H, s)

Step 5

3-[4-(5-bromopyridin-3-yl)pyrimidin-2-ylamino]-4-methylaniline

To 807 mg of 2-[4-(5-bromopyridin-3-yl)pyrimidin-2-ylamino]-1-methyl-4-nitrobenzene obtained in the step 4, 5 ml of concentrated hydrochloric acid was added and a solution of 2.36 g of tin chloride(II) dihydrate in 3.5 ml of concentrated hydrochloric acid was added while stirring with heating at 55° C. The mixture was gradually heated up to 100° C. and further stirred with heating at 100° C. for 15 minutes. The reaction solution was air-cooled and water was added, and then alkalified with an aqueous 10% sodium hydroxide solution. After the addition of chloroform and stirring for a while, insolubles were removed by filtration and the aqueous layer was separated. The aqueous layer was further extracted with chloroform and the organic layers were combined and, after drying over anhydrous magnesium sulfate, the solvent was distilled off under reduced pressure. The residue was purified by silica gel column chromatography to obtain a crude product. The crude product was crystallized by adding diethyl ether-ethyl acetate and the crystal was collected by filtration to obtain 528 mg of the objective compound as a yellow crystal.

Melting point: 129.5-130° C. $^1$H-NMR (CDCl$_3$) δ: 2.26 (3H, s), 3.64 (2H, br), 6.44 (1H, dd), 6.99 (1H, s), 7.01 (1H, d), 7.13 (1H, d), 7.59 (1H, d), 8.53 (2H, m), 8.78 (1H, s), 9.15 (1H, s)

REFERENCE EXAMPLE 10

3-[4-(1,2-dihydropyridazin-4-yl)pyrimidin-2-ylamino]-4-methylaniline

Step 1

4-acetylpyridazine

To 3.55 g of malonic acid monoethyl ester potassium salt and 2.21 g of magnesium chloride, 12 ml of N,N-dimethylformamide was added and the mixture was stirred with heating at 60° C. for 4 hours (reaction solution 1). Separately, a reaction solution (reaction solution 2) was prepared by stirring 2.07 g of 4-pyridazinecarboxylic acid (J. Heterocyclic Chem., 1990, 27, 579-582.) and 2.95 g of 1,1'-carbonylbis-1H-imidazole in 12 ml of N,N-dimethylformamide at room temperature for 4 hours and the reaction solution was added to the reaction solution 1, followed by stirring at room temperature for 26 hours. To the reaction solution, diethyl ether was added and the mixture was neutralized with 50 ml of 1N hydrochloric acid. The aqueous layer was separated and the aqueous layer was further extracted four times with diethyl ether. The organic layers were combined and, after drying over anhydrous magnesium sulfate, the solvent was distilled off under reduced pressure. To the resulting oily product, dimethyl sulfoxide-water (5 ml-0.4 ml) was added, followed by stirring with heating at 150 to 160° C. for 2 hours. The solvent was distilled off under reduced pressure and the residue was purified by silica gel column chromatography. The resulting crude crystal was washed with diisopropyl ether and then collected by filtration to obtain 429 mg of the objective compound as a pale yellow crystal.

Melting point: 66.5-67.5° C. $^1$H-NMR (CDCl$_3$) δ: 2.70 (3H, s), 7.87 (1H, dd), 9.49 (1H, dd), 9.62 (1H, t)

Step 2

3-(dimethylamino)-1-(4-pyridazinyl)-2-propen-1-one

This compound was prepared by version of the method described in the document (Japanese Unexamined Patent Publication (Kokai) No. 6-87834). To 410 mg of 4-acetylpyridazine obtained in the step 1, 440 mg of N,N-dimethylformamide dimethyl acetal was added and the mixture was heated at reflux for one hour. After air-cooling, the reaction solution was directly purified by silica gel column chromatography. The resulting crude crystal was washed with diethyl ether and then collected by filtration to obtain 341 mg of the objective compound as an orange crystal.

Melting point: 136-138° C. $^1$H-NMR (CDCl$_3$) δ: 3.01 (3H, s), 3.24 (3H, s), 5.66 (1H, d), 7.85 (1H, dd), 7.92 (1H, d), 9.32 (1H, dd), 9.55 (1H, t)

Step 3

1-methyl-4-nitro-2-[4-(4-pyridazinyl)pyrimidin-2-ylamino]benzene

To 327 mg of 3-(dimethylamino)-1-(4-pyridazinyl)-2-propen-1-one obtained in the step 2 and 359 mg of 1-(2-methyl-5-nitrophenyl)guanidine obtained in the step 2 of Reference Example 6, 4 ml of 2-propanol was added and the mixture was heated at reflux for 22 hours. The reaction solution was air-cooled and the deposited crystal was collected by filtration, and then washed in turn with 2-propanol and diethyl ether to obtain 437 mg of the objective compound as a pale yellow crystal.

Melting point: 0.243-245° C. $^1$H-NMR (DMSO-d$_6$) δ: 2.43 (3H, s), 7.53 (1H, d), 7.73 (1H, d), 7.93 (1H, dd), 8.29 (1H, dd), 8.73 (2H, m), 9.44 (2H, m), 9.88 (1H, s)

Step 4

3-[4-(1,2-dihydropyridazin-4-yl)pyrimidin-2-ylamino]-4-methylaniline

To 413 mg of 1-methyl-4-nitro-2-[4-(4-pyridazinyl)pyrimidin-2-ylamino]benzene obtained in the step 3, 3 ml of concentrated hydrochloric acid was added and a solution of 1.51 g of tin chloride(II) dihydrate in 2 ml of concentrated hydrochloric acid was added while stirring with heating at 55° C. The mixture was gradually heated up to 100° C. and further stirred with heating at 100° C. for 25 minutes. The reaction solution was air-cooled and, after adding water, the solution was alkalified with an aqueous 10% sodium hydroxide solution. After the addition of chloroform and stirring for a while, insolubles were removed by filtration and the aqueous layer was separated. The aqueous layer was further extracted with chloroform and the organic layers were combined and, after drying over anhydrous magnesium sulfate, the solvent was distilled off under reduced pressure. The residue was purified by silica gel column chromatography to obtain 38 mg of the objective compound as a pale yellow amorphous.

$^1$H-NMR (CDCl$_3$) δ: 2.24 (3H, s), 4.96 (2H, s), 6.37 (1H, dd), 6.58 (1H, dd), 6.73 (1H, t), 6.79 (1H, s), 6.80 (1H, d), 6.97 (1H, d), 7.41 (1H, t), 7.70 (1H, d), 8.27 (1H, d)

REFERENCE EXAMPLE 11

4-methyl-3-[4-(3-pyridazinyl)pyrimidin-2-ylamino]aniline

Step 1

3-(dimethylamino)-1-(3-pyridazinyl)-2-propen-1-one

This compound was prepared by version of the method described in the document (Japanese Unexamined Patent Publication (Kokai) No. 6-87834). To 762 mg of 3-acetylpyridazine (Arzneim.-Forsch./Drug Res., 1989, 39 (2), 1196-1201), 818 mg of N,N-dimethylformamide dimethyl acetal was added and the mixture was heated at reflux for 1.5 hours. After air cooling, the reaction solution was directly purified by silica gel column chromatography. The resulting crude crystal was washed with diisopropyl ether and then collected by filtration to obtain 945 mg of the objective compound as a yellowish brown crystal.

Melting point: 102-105° C. $^1$H-NMR (CDCl$_3$) δ: 3.04 (3H, s), 3.22 (3H, s), 6.69 (1H, d), 7.61 (1H, dd), 7.99 (1H, d), 8.27 (1H, dd), 9.24 (1H, dd)

Step 2

1-methyl-4-nitro-2-[4-(3-pyridazinyl)pyrimidin-2-ylamino]benzene 800 mg of 3-(dimethylamino)-1-(3-pyridazinyl)-2-propen-1-one obtained in the step 1 and 876 mg of 1-(2-methyl-5-nitrophenyl)guanidine obtained in the step 2 of Reference Example 6 were stirred with heating at 120° C. for 3 hours. The solidified reaction solution was crystallized by adding 2-propanol and then washed in turn with 2-propanol and diethyl ether to obtain 1.21 g of the objective compound as a dark brown crystal.

Melting point: 275-277° C. $^1$H-NMR (CF$_3$COOD) δ: 2.45 (3H, s), 7.56 (1H, br), 8.18 (3H, br), 8.57 (1H, br), 8.75 (2H, br), 9.18 (1H, br), 9.79 (1H, br)

Step 3

4-methyl-3-[4-(3-pyridazinyl)pyrimidin-2-ylamino]aniline 754 m of 1-methyl-4-nitro-2-[4-(3-pyridazinyl)pyrimidin-2-ylamino]benzene obtained in the step 2 was suspended in 40 ml of methanol and 4.21 g of sodium dithionite and 3.05 g of sodium hydrogen carbonate were added, and then the mixture was heated at reflux for 5 hours. After the reaction solution was air-cooled, insolubles were removed by filtration and the solvent was distilled off under reduced pressure. To the residue, water and chloroform were added to separate the aqueous layer, and then the aqueous layer was extracted three times with chloroform. The organic layers were combined, washed in turn with water and saturated saline and then dried over anhydrous magnesium sulfate. The solvent was distilled off under reduced pressure. The residue was purified by silica gel column chromatography to obtain 247 mg of the objective compound as a yellow oily product.

$^1$H-NMR (CDCl$_3$) δ: 2.26 (3H, s), 3.65 (2H, br), 6.44 (1H, dd), 6.95 (1H, br), 7.02 (1H, d), 7.54 (1H, d), 7.63 (1H, dd), 8.02 (1H, d), 8.50 (1H, dd), 8.62 (1H, d), 9.27 (1H, dd)

REFERENCE EXAMPLE 12

4-methyl-3-[4-(3-pyridyl)pyridin-2-ylamino]aniline

Step 1

2-[(4-chloro)pyridin-2-ylamino]-1-methyl-4-nitrobenzene

This compound was prepared by version of the method described in the document (J. Org. Chem., 1996, 61, 7240-7241). To 2.00 g of 2,4-dichloropyridine (Recl. Trav. Chim. Pays-Bas., 1950, 69, 673-699.), 2.26 g of 2-methyl-5-nitroaniline, 121 mg of palladium(II) acetate, 336 mg of (±)-2,2'-bis(diphenylphosphino)-1,1'-binaphthyl [(±)-BINAP] and 6.16 g of cesium carbonate, 120 ml of toluene was added, and then the mixture was stirred with heating at 70° C. for 23 hours under an argon atmosphere. After insolubles were removed by filtration, the solvent was distilled off under reduced pressure. The residue was purified by silica gel column chromatography to obtain 2.11 g of a crude product. The crude product was washed with diethyl ether to obtain 1.22 g of the objective compound as a yellow crystal.

Melting point: 130-133° C. $^1$H-NMR (CDCl$_3$) δ: 2.38 (3H, s), 6.40 (1H, br), 6.74 (1H, d), 6.85 (1H, dd), 7.38 (1H, d), 7.90 (1H, dd), 8.15 (1H, d), 8.57 (1H, d)

Step 2

1-methyl-4-nitro-2-[4-(3-pyridyl)pyridin-2-ylamino]benzene

To 20 ml of deaerated tetrahydrofuran-water (1:1), 264 mg of 2-[(4-chloro)pyridin-2-ylamino]-1-methyl-4-nitrobenzene obtained in the step 1, 162 mg of diethyl(3-pyridyl)borane, 470 mg of potassium carbonate and 173 mg of tetrakis(triphenylphosphine)palladium(0) were added in turn and the mixture was stirred with heating at 80° C. for 44 hours under an argon atmosphere. The reaction solution was diluted with ethyl acetate to separate the aqueous layer, and then the aqueous layer was further extracted three times with ethyl acetate. The organic layers were combined, washed in turn with water and saturated saline and dried over anhydrous magnesium sulfate, and then the solvent was distilled off under reduced pressure. The residue was purified by silica gel column chromatography to obtain 247 mg of a crude product. The crude product was crystallized by adding chloroform-methanol and then collected by filtration to obtain 143 mg of the objective compound as an orange crystal.

Melting point: 170-173° C. $^1$H-NMR (CDCl$_3$) δ: 2.43 (3H, s), 6.49 (1H, br), 6.99 (1H, s), 7.07 (1H, dd), 7.41 (2H, m), 7.87 (2H, m), 8.37 (1H, d), 8.68 (1H, dd), 8.69 (1H, s), 8.86 (1H, d)

Step 3

4-methyl-3-[4-(3-pyridyl)pyridin-2-ylamino]aniline

To 126 mg of 1-methyl-4-nitro-2-[4-(3-pyridyl)pyridin-2-ylamino]benzene obtained in the step 2, 1 ml of concentrated hydrochloric acid was added and a solution of 465 mg of tin chloride(II) dihydrate in 1 ml of concentrated hydrochloric acid was added while stirring with heating at 60° C. The mixture was gradually heated up to 100° C. and further stirred with heating at 100° C. for 40 minutes. After the reaction solution was air-cooled, water was added and the solution was alkalified with an aqueous 10% sodium hydroxide solution. The solution was extracted three times with ethyl acetate and dried over anhydrous magnesium sulfate, and then the solvent was distilled off under reduced pressure. The resulting crude crystal was washed with a small amount of chloroform and then collected by filtration to obtain 93 mg of the objective compound as a pale yellow crystal.

Melting point: 183-186° C. $^1$H-NMR (CDCl$_3$) δ: 2.19 (3H, s), 3.60 (2H, br), 6.37 (1H, br), 6.47 (1H, dd), 6.82 (1H, s), 6.88 (1H, d), 6.91 (1H, dd), 7.04 (1H, d), 7.37 (1H, dd), 7.83 (1H, dt), 8.26 (1H, d), 8.64 (1H, dd), 8.81 (1H, d)

REFERENCE EXAMPLE 13

4-methyl-3-[4-(5-pyrimidinyl)pyridin-2-ylamino]aniline

Step 1

1-methyl-4-nitro-2-[4-(5-pyrimidinyl)pyridin-2-ylamino]benzene

In the same manner as in Reference Example 12 (step 2), except that dihydroxy(5-pyrimidinyl)borane was used in place of diethyl(3-pyridyl)borane, the objective compound was prepared. The crude crystal obtained by purification with silica gel column chromatography was washed with diethyl ether.

Yellow Crystal

Melting point: 230-232° C. $^1$H-NMR (DMSO-d$_6$) δ: 2.42 (3H, s), 7.31 (1H, dd), 7.47 (2H, m), 7.80 (1H, dd), 8.33 (1H, d), 8.61 (1H, s), 8.94 (1H, d), 9.19 (2H, s), 9.30 (1H, s)

Step 2

4-methyl-3-[4-(5-pyrimidinyl)pyridin-2-ylamino]aniline 163 mg of 1-methyl-4-nitro-2-[4-(5-pyrimidinyl)pyridin-2-ylamino]benzene obtained in the step 1 was dissolved in 32 ml of tetrahydrofuran-methanol (1:1) and 98 mg of 10% palladium-carbon was added. Furthermore, 284 mg of ammonium formate was added and the mixture was heated at reflux at a bath temperature of 90° C. for 40 minutes. The catalyst was removed by filtration and the solvent in the filtrate was distilled off under reduced pressure. To the residue, water and ethyl acetate were added to separate the aqueous layer. The aqueous layer was further extracted with ethyl acetate. The organic layers were combined and dried over anhydrous magnesium sulfate, and then the solvent was distilled off under reduced pressure. The residue was purified by silica gel column chromatography to obtain 149 mg of the objective compound as a pale yellow crystal.

Melting point: 179-180° C. $^1$H-NMR (DMSO-$d_6$) δ: 2.19 (3H, s), 3.62 (2H, br), 6.39 (1H, br), 6.49 (1H, dd), 6.76 (1H, s), 6.83 (1H, d), 6.90 (1H, dd), 7.06 (1H, d), 8.31 (1H, d), 8.90 (2H, s), 9.25 (1H, s)

REFERENCE EXAMPLE 14

4-methyl-3-[2-(3-pyridyl)pyridin-6-ylamino]aniline

Step 1

2-bromo-6-(3-pyridyl)pyridine

This compound was prepared by version of the method described in the document (Chem. Pharm. Bull., 1985, 33(11), 4755-4763). To 40 ml of tetrahydrofuran, 1.76 g of diethyl(3-pyridyl)borane, 5.92 g of 2,6-dibromopyridine, 1.99 g of tetra-n-butylammonium bromide, 692 mg of tetrakis(triphenylphosphine)palladium(0) and 1.87 g of ground potassium hydroxide were added in turn and the mixture was heated at reflux for three hours under an argon atmosphere. After air cooling, the reaction solution was diluted with ethyl acetate and insolubles were removed by, filtration. The solvent in the filtrate was distilled off under reduced pressure and ethyl acetate and saturated saline were added to the residue to separate the aqueous layer. The organic layer was dried over anhydrous magnesium sulfate and the solvent was distilled off under reduced pressure. The residue was purified by silica gel column chromatography to obtain 1.26 g of the objective compound as a pale yellow crystal.

$^1$H-NMR (CDCl$_3$) δ: 7.34-7.51 (2H, m), 7.62-7.75 (2H, m), 8.34 (1H, dt), 8.67 (1H, dd), 9.17 (1H, d)

Step 2

1-methyl-4-nitro-2-[2-(3-pyridyl)pyridin-6-ylamino]benzene

This compound was prepared by version of the method described in the document (J. Org. Chem., 2000, 65, 1144-1157). To 940 mg of 2-bromo-6-(3-pyridyl)pyridine obtained in the step 1, 730 mg of 2-methyl-5-nitroaniline, 37 mg of tris(dibenzylideneacetone)dipalladium(0), 75 mg of (±)-2,2'-bis(diphenylphosphino)-1,1'-binaphthyl [(±)-BINAP] and 1.82 mg of cesium carbonate, 12 ml of toluene was added and the mixture was stirred with heating at 110° C. for 24 hours under an argon atmosphere. After air cooling, the reaction solution was diluted with ethyl acetate and insolubles were removed by filtration. The solvent in the filtrate was distilled off under reduced pressure and the residue was crystallized by adding diethyl ether. The resulting crystal was collected by filtration and then washed with ethyl acetate-diethyl ether to obtain 646 mg of the objective compound as a yellow crystal.

Melting point: 148-150° C. $^1$H-NMR (CDCl$_3$) δ: 2.42 (3H, s), 6.53 (1H, br), 6.80 (1H, d), 7.35 (2H, d), 7.44 (1H, dd), 7.69 (1H, m), 7.83 (1H, dd), 8.44 (1H, dt), 8.65 (1H, dd), 9.09 (1H, d), 9.20 (1H, d)

Step 3

4-methyl-3-[2-(3-pyridyl)pyridin-6-ylamino]aniline 500 mg of 1-methyl-4-nitro-2-[2-(3-pyridyl)pyridin-6-ylamino]benzene obtained in the step 2 was dissolved in 10 ml of ethanol and 1.05 g of zinc (powder), 430 mg of ammonium chloride and 0.46 ml of acetic acid were added, and then the mixture was stirred with heating at 80° C. for 30 minutes. The catalyst was removed by filtration and the solvent in the filtrate was distilled off under reduced pressure. To the residue, ethyl acetate and an aqueous saturated sodium hydrogen carbonate solution were added to separate the aqueous layer. The aqueous layer was further extracted three times with ethyl acetate. The organic layers were combined and dried over anhydrous magnesium sulfate, and then the solvent was distilled off under reduced pressure to obtain 114 mg of the objective compound as a pale yellow amorphous.

$^1$H-NMR (CDCl$_3$) δ: 2.19 (3H, s), 3.40 (2H, br), 6.37 (1H, br), 6.45 (1H, dd), 6.68 (1H, d), 6.91 (1H, d), 7.03 (1H, d), 7.16 (1H, d), 7.38 (1H, dd), 7.56 (1H, t), 8.29 (1H, dt), 8.62 (1H, dt), 9.19 (1H, d)

REFERENCE EXAMPLE 15

4-methyl-3-[3-(3-pyridyl)pyridin-5-ylamino]aniline

Step 1

3-bromo-5-(3-pyridyl)pyridine

In the same manner as in Reference Example 14 (step 1), except that 3,5-dibromopyridine was used in place of 2,6-dibromopyridine, the objective compound was prepared.

Colorless Crystal $^1$H-NMR (CDCl$_3$) δ: 7.44 (1H, m), 7.88 (1H, m), 8.04 (1H, t), 8.68-8.77 (3H, m), 8.84 (1H, dd)

Step 2

1-methyl-4-nitro-2-[3-(3-pyridyl)pyridin-5-ylamino]benzene

This compound was prepared by version of the method described in the document (J. Org. Chem., 1996, 61, 7240-7241). To 25 mg of (±)-2,2'-bis(diphenylphosphino)-1,1'-binaphthyl [(±)-BINAP], 2 ml of toluene was added and (±)-BINAP was dissolved by stirring with heating at 80° C. under an argon atmosphere. The solution was once air-cooled to room temperature and 6 mg of palladium(II) acetate was added and, stirring for one minute, 620 mg of 3-bromo-5-(3-pyridyl)pyridine obtained in the step 1, 482 mg of 2-methyl-5-nitroaniline, 1.20 g of cesium carbonate and 2 ml (total 4 ml) of toluene were added, followed by stirring with heating at 80° C. for 18 hours and further heating at 100° C. for 24 hours under an argon atmosphere. After air cooling, the reaction solution was diluted with ethyl acetate and insolubles were removed by filtration. The solvent in the filtrate was distilled off under reduced pressure and the residue was purified by silica gel column chromatography to obtain 108 mg of the objective compound as a yellow crystal.

Melting point: 0.195-198° C. $^1$H-NMR (CDCl$_3$) δ: 2.41 (3H, s), 5.76 (1H, br), 7.39 (1H, br), 7.42 (1H, ddd), 7.54 (1H, dd), 7.83 (1H, dd), 7.88 (1H, m), 8.09 (1H, d), 8.43 (1H, d), 8.50 (1H, d), 8.67 (1H, dd), 8.83 (1H, d)

Step 3

4-methyl-3-[3-(3-pyridyl)pyridin-5-ylamino]aniline

In the same manner as in Reference Example 12 (step 3), except that 1-methyl-4-nitro-2-[3-(3-pyridyl)pyridin-5-ylamino]benzene obtained in the step 2 was used in place of 1-methyl-4-nitro-2-[4-(3-pyridyl)pyridin-2-ylamino]benzene, the objective compound was prepared. The residue obtained by concentration under reduced pressure was not further purified.

Pale Brown Oily Product $^1$H-NMR (CDCl$_3$) δ: 2.16 (3H, s), 3.34 (2H, br), 5.78 (1H, br), 6.40 (1H, dd), 6.61 (1H, d), 7.01 (1H, d), 7.33-7.40 (2H, m), 7.81 (1H, dt), 8.28 (1H, d), 8.30 (1H, d), 8.61 (1H, dd), 8.78 (1H, d)

REFERENCE EXAMPLE 16

4-methyl-3-[3-(3-pyridyl)phenylamino]aniline

Step 1

2-(3-bromophenylamino)-1-methyl-4-nitrobenzene

This compound was prepared by version of the method described in the document (J. Org. Chem., 2000, 65, 1144-0.1157). To 1.00 g of 1-bromo-3-iodobenzene, 591 mg of 2-methyl-5-nitroaniline, 32 mg of tris(dibenzylideneacetone)dipalladium(0), 66 mg of (±)-2,2'-bis(diphenylphosphino)-1,1'-binaphthyl [(±)-BINAP] and 1.61 g of cesium carbonate, 14 ml of toluene was added and the mixture was stirred with heating at 100° C. for 36 hours under an argon atmosphere. After air cooling, insolubles were removed by filtration and the solvent in the filtrate was distilled off under reduced pressure. The residue was purified by silica gel column chromatography to obtain 256 mg of the objective compound as an orange crystal.

Melting point: 114-116° C. $^1$H-NMR (CDCl$_3$) δ: 2.34 (3H, s), 5.52 (1H, br), 6.99 (1H, m), 7.14-7.21 (3H, m), 7.33 (1H, d), 7.77 (1H, dd), 8.02 (1H, d)

Step 2

1-methyl-4-nitro-2-[3-(3-pyridyl)phenylamino]benzene

In the same manner as in Reference Example 12 (step 2), except that 2-(3-bromophenylamino)-1-methyl-4-nitrobenzene obtained in the step 1 was used in place of 2-[(4-chloro)pyridin-2-ylamino]-1-methyl-4-nitrobenzene, the objective compound was prepared. The crude product obtained purified by silica gel column chromatography was crystallized by adding ethyl acetate.

Yellow Crystal

Melting point: 162-165° C. $^1$H-NMR (DMSO-d$_6$) δ: 2.36 (3H, s), 7.17 (1H, d), 7.30 (1H, d), 7.40-7.70 (5H, m), 7.93-7.95 (2H, m), 8.02 (1H, d), 8.57 (1H, d), 8.85 (1H, s)

Step 3

4-methyl-3-[3-(3-pyridyl)phenylamino]aniline

In the same manner as in Reference Example 12 (step 3), except that 1-methyl-4-nitro-2-[3-(3-pyridyl)phenylamino]benzene obtained in the step 2 was used in place of 1-methyl-4-nitro-2-[4-(3-pyridyl)pyridin-2-ylamino]benzene, the objective compound was prepared. The residue obtained by concentration under reduced pressure was not further purified.

Pale Yellow Oily Product $^1$H-NMR (CDCl$_3$) δ: 2.17 (3H, s), 3.50 (2H, br), 5.48 (1H, br), 6.33 (1H, dd), 6.64 (1H, d), 6.97-7.15 (4H, m), 7.31-7.39 (2H, m), 7.85 (1H, dt), 8.57 (1H, dd), 8.82 (1H, d)

REFERENCE EXAMPLE 17

4-methyl-3-[2-(3-pyridyl)pyrazin-6-ylamino]aniline

Step 1

2-[(2-chloro)pyrazin-6-ylamino]-1-methyl-4-nitrobenzene

In the same manner as in Reference Example 12 (step 1), except that 2,6-dichloropyrazine was used in place of 2,4-dichloropyridine, the objective compound was prepared.

Yellow Crystal $^1$H-NMR (CDCl$_3$) δ: 2.42 (3H, s), 6.44 (1H, s), 7.43 (1H, d), 7.97 (1H, dd), 8.09 (2H, d), 8.58 (1H, d)

Step 2

1-methyl-4-nitro-2-[2-(3-pyridyl)pyrazin-6-ylamino]benzene

To 64 ml of deaerated tetrahydrofuran-water (1:1), 790 mg of 2-[(2-chloro)pyrazin-6-ylamino]-1-methyl-4-nitrobenzene obtained in the step 1, 406 mg of dihydroxy(3-pyridyl)borane, 1.41 g of potassium carbonate and 520 mg of tetrakis(triphenylphosphine)palladium(0) were added in turn and the mixture was heated at reflux at a bath temperature of 100° C. for 3 hours under an argon atmosphere. 32 ml of tetrahydrofuran-water (1:1) was added and the mixture was further heated at reflux for 3 hours and then allowed to stand at room temperature overnight. The deposited insolubles were collected by filtration and extracted and washed with methanol, and then the solvent in the filtrate was distilled off under reduced pressure. To the residue, diethyl ether was added and, after stirring, the crystal was collected by filtration and then washed with methanol to obtain 270 mg of the objective compound as an amorphous.

$^1$H-NMR (DMSO-d$_6$) δ: 2.45 (3H, s), 7.51 (1H, d), 7.55 (1H, d), 7.85 (1H, dd), 8.45 (1H, d), 8.50 (1H, s), 8.65 (1H, d), 8.74 (1H, s), 9.04 (1H, s), 9.20 (1H, d), 9.29 (1H, s)

Step 3

4-methyl-3-[2-(3-pyridyl)pyrazin-6-ylamino]aniline 107 mg of 1-methyl-4-nitro-2-[2-(3-pyridyl)pyrazin-6-ylamino]benzene obtained in the step 2 was dissolved in 10 ml of methanol (portion was not dissolved and suspended) and 16 mg of 10% palladium-carbon was added. Furthermore, 221 mg of ammonium formate was added, followed by stirring with heating at a bath temperature of 50° C. for 15 hours. The catalyst was removed by filtration and the solvent in the filtrate was distilled off under reduced pressure. To the residue, water and ethyl acetate were added to separate the aqueous layer. The aqueous layer was further extracted with ethyl acetate. The organic layers were combined and dried over anhydrous magnesium sulfate, and then the solvent was distilled off under reduced pressure to obtain 95 mg of the objective compound.

$^1$H-NMR (CDCl$_3$) δ: 2.22 (3H, s), 6.39 (1H, s), 6.48 (1H, dd), 6.99 (1H, d), 7.06 (1H, d), 7.43 (1H, ddd), 8.10 (1H, s), 8.28 (1H, ddd), 8.43 (1H, s), 8.68 (1H, dd), 9.23 (1H, dd)

REFERENCE EXAMPLE 18

4-methyl-3-[5-(3-pyridyl)-1,2,4-triazin-3-ylamino]aniline

Step 1

3-methylthio-5-(3-pyridyl)-1,2,4-triazine

First, (3-pyridyl)glyoxal hydrobromide was prepared by version of the method described in the document (Heterocycles, 1990, 31(12), 2163-2172). 5.00 g of 3-(bromoacetyl)pyridine hydrobromide (J. Heterocyclic. Chem., 1969, 6(6), 891-900.) was suspended in 30 ml of methanol and 3.40 g of pyridine N-oxide was added under ice-cool stirring, followed by stirring at room temperature for 26 hours after removing an ice bath. This compound was used for the subsequent reaction without being isolated. Then, 3-methylthio-5-(3-pyridyl)-1,2,4-triazine was prepared by version of the method described in the document (J. Med. Chem., 1979, 22 (6), 671-677). To the solution above, 4.18 g of S-methylthiosemicarbazide hydroiodide (Heterocycles, 1979, 12 (6), 745-749) and 1.51 g of sodium hydrogen carbonate were added under ice-cool stirring and 6 ml of water was added and, after slowly returning the temperature to room temperature, the mixture was stirred at room temperature for 57 hours. The reaction solution was alkalified by adding a cold aqueous saturated sodium hydrogen carbonate solution, extracted twice with ethyl acetate and dried over anhydrous magnesium sulfate, and then the solvent was distilled off under reduced pressure. The residue was purified by silica gel column chromatography to obtain 1.37 g of a crude product. The crude product was washed with warmed diisopropyl ether to obtain 1.13 g of the objective compound as a pale yellowish green crystal.

Melting point: 98-102° C. $^1$H-NMR (CDCl$_3$) δ: 2.75 (3H, s), 7.52 (1H, ddd), 8.48 (1H, ddd), 8.84 (1H, dd), 9.37 (1H, t), 9.43 (1H, s)

Step 2

3-methylsulfinyl-5-(3-pyridyl)-1,2,4-triazine 3.00 g of 3-methylthio-5-(3-pyridyl)-1,2,4-triazine obtained in the step 1 was dissolved in 50 ml of dichloromethane and 5.76 g of 70% m-chloroperbenzoic acid was added under ice-cool stirring. After stirring under ice cooling for 20 minutes, the temperature was returned to room temperature and 1.5 g of magnesium sulfate and 10 g of NH-Silica Gel (Chromatorex NH-DM1020, manufactured by Fuji Silysia Chemical Co., Ltd.) was added. After stirring at room temperature for 10 minutes, insolubles were removed by filtration and the solvent in the filtrate was distilled off under reduced pressure. The residue was purified by silica gel column chromatography to obtain 1.65 g of a crude product. The crude product was washed with 2-propanol-diethyl ether to obtain 1.07 g of the objective compound as a pale brown crystal.

Melting point: 150-152° C. $^1$H-NMR (CDCl$_3$) δ: 3.17 (3H, s), 7.58 (1H, dd), 8.67 (1H, dd), 8.97 (1H, dd), 9.47 (1H, d), 9.85 (1H, s)

Step 3

N-(5-amino-2-methylphenyl)acetamide 3.00 g of N-(2-methyl-5-nitrophenyl)acetamide (Can. J. Chem., 1984, 62, 1292-1296.) was suspended in 100 ml of ethanol and 600 mg of 10% palladium-carbon was added, and then the mixture was hydrogenated at room temperature under 4 atm for 3 hours. The catalyst was removed by filtration and the solvent in the filtrate was distilled off under reduced pressure to obtain 2.50 g of a crude product. The crude product was washed with warmed diisopropyl ether to obtain 2.37 g of the objective compound as a pale green crystal.

Melting point: 136-139° C. $^1$H-NMR (D$_2$O) δ: 2.00 (3H, s), 3.38 (3H, s), 4.84 (2H, br), 6.29 (1H, dd), 6.67 (1H, d), 6.80 (1H, d), 9.01 (1H, br)

Step 4

4-methyl-3-[5-(3-pyridyl)-1,2,4-triazin-3-ylamino]aniline 671 mg of N-(5-amino-2-methylphenyl)acetamide obtained in the step 3 was dissolved in 40 ml of tetrahydrofuran and 180 mg of 60% sodium hydride was added under ice-cool stirring. After stirring under ice cooling for 5 minutes, the temperature was returned to room temperature, followed by stirring for 30 minutes and 900 mg of 3-methylsulfinyl-5-(3-pyridyl)-1,2,4-triazine obtained in the step 2 was added. After stirring at room temperature for 3.5 hours, the reaction solution was mixed with ice water, extracted twice with didhloromethane and dried over anhydrous magnesium sulfate, and then the solvent was distilled off under reduced pressure. The residue was purified by silica gel column chromatography to obtain 733 mg of 4-methyl-3-{N-acetyl-N-[5-(3-pyridyl)-1,2,4-triazin-3-yl]amino}aniline as an intermediate. The above compound was dissolved in 10 ml of methanol and 2.0 ml of an aqueous 1N sodium hydroxide solution was added, followed by stirring at room temperature for 45 minutes. The reaction solution was mixed with water, extracted twice with ethyl acetate and dried over anhydrous magnesium sulfate, and then the solvent was distilled off under reduced pressure. The residue was purified by silica gel column chromatography to obtain 478 mg of the objective compound as a yellowish brown amorphous.

$^1$H-NMR (CDCl$_3$) δ: 2.27 (3H, s), 3.5-3.9 (2H, br), 6.46 (1H, dd), 7.02 (1H, d), 7.38 (1H, br), 7.44-7.51 (2H, m), 8.38 (1H, dt), 8.79 (1H, dd), 9.19 (1H, s), 9.32 (1H, d)

REFERENCE EXAMPLE 19

3-methyl-4-(4-methylpiperazin-1-ylmethyl)benzoyl chloride dihydrochloride

Step 1

1-(4-methoxy-2-methylbenzoyl)-4-methylpiperazine

To 3.32 g of 4-methoxy-2-methylbenzoic acid, 5.75 g of 1-(3-dimethylaminopropyl)-3-ethylcarbodiimide hydrochloride and 4.05 g of 1-hydroxybenzotriazole, 10 ml of N,N-dimethylformamide was added. Under stirring at room temperature, a solution of 2.00 g of N-methylpiperazine in 10 ml of N,N-dimethylformamide and a solution of 1.52 g of triethylamine in 10 ml of N,N-dimethylformamide were added dropwise in turn, followed by stirring at room temperature for 15 hours. After the solvent was distilled off under reduced pressure, an aqueous saturated sodium hydrogen carbonate solution was added to the residue and the solution was extracted twice with ethyl acetate. After drying over anhydrous magnesium sulfate, the solvent was distilled off under reduced pressure. The residue was purified by silica gel column chromatography to obtain 4.25 g of the objective compound as a pale yellow oily product.

$^1$H-NMR (CDCl$_3$) δ: 2.30 (3H, s), 2.30 (2H, br), 2.31 (3H, s), 2.47 (2H, br), 3.27 (2H, br), 3.80 (3H, s), 3.80 (2H, br), 6.73 (1H, d), 6.75 (1H, s), 7.09 (1H, dd)

Step 2

1-(4-hydroxy-2-methylbenzoyl)-4-methylpiperazine 4.89 g of 1-(4-methoxy-2-methylbenzoyl)-4-methylpiperazine obtained in the step 1 was dissolved in 150 ml of dichloromethane and a solution of 9.87 g of boron tribromide in 100 ml of dichloromethane was added dropwise under ice-cool stirring. After stirring under ice cooling for one hour, the temperature was returned to room temperature and the mixture was further stirred for 15 hours. The reaction solution was ice-cooled and alkalified by adding 50 ml of water and 150 ml of an aqueous saturated sodium hydrogen carbonate solution, and then insolubles were removed by filtration. The filtrate was extracted with chloroform and dried over anhydrous magnesium sulfate, and then the solvent was distilled off under reduced pressure. The residue was purified by silica gel column chromatography to obtain 2.20 g of the objective compound as a pale yellow crystal.

Melting point: 167-168° C. $^1$H-NMR (CDCl$_3$) δ: 2.18 (3H, s), 2.32 (3H, s), 2.32 (2H, br), 2.50 (2H, br), 3.30 (2H, br), 3.83 (2H, br), 4.17 (1H, br), 6.52 (1H, s), 6.54 (1H, d), 6.94 (1H, d)

Step 3

3-methyl-4-(4-methylpiperazin-1-ylmethyl)phenol 1.96 g of 1-(4-hydroxy-2-methylbenzoyl)-4-methylpiperazine obtained in the step 2 was dissolved in 35 ml of tetrahydrofuran and 0.317 g of lithium aluminum hydride was added by several portions under ice-cool stirring. After stirring at room temperature for 4 hours, the mixture was ice-cooled again and 0.317 g of lithium aluminum hydride was added by several portions under ice-cool stirring, followed by stirring at room temperature for 15 hours. The reaction solution was ice-cooled and hydrous tetrahydrofuran was added and, after decomposing lithium aluminum hydride, insolubles were removed by filtration. The solvent in the filtrate was distilled off and the residue was crystallized by adding acetone to obtain 1.10 g of the objective compound as a colorless crystal.

Melting point: 174-176° C. $^1$H-NMR (CDCl$_3$) δ: 2.28 (3H, s), 2.29 (3H, s), 2.51 (8H, br), 3.39 (2H, s), 6.50 (1H, dd), 6.54 (1H, d), 7.03 (1H, d)

Step 4

3-methyl-4-(4-methylpiperazin-1-ylmethyl)phenyl trifluoromethanesulfonate 660 mg of 3-methyl-4-(4-methylpiperazin-1-ylmethyl)phenol obtained in the step 3 was dissolved in 6.6 ml of pyridine and 1.86 g of anhydrous trifluoromethanesulfonic acid was added under ice-cool stirring, followed by stirring at room temperature for 12 hours. The reaction solution was mixed with ice water, extracted three times with ethyl acetate and then washed with water. After drying over anhydrous magnesium sulfate, the solvent was distilled off under reduced pressure. The residue was purified by silica gel column chromatography to obtain 535 mg of the objective compound as a pale yellow oily product.

$^1$H-NMR (CDCl$_3$) δ: 2.31 (3H, s), 2.38 (3H, s), 2.47 (8H, br), 3.45 (2H, s), 7.04 (1H, d), 7.06 (1H, s), 7.35 (1H, d)

Step 5

Methyl 3-methyl-4-(4-methylpiperazin-1-ylmethyl)benzoate 705 mg of 3-methyl-4-(4-methylpiperazin-1-ylmethyl)phenyl trifluoromethanesulfonate obtained in the step 4 was dissolved in solvent mixture of 8.40 ml of dimethyl sulfoxide, 4.96 ml of methanol, 2.68 ml of 1,2-dichloroethane and 0.76 ml of triethylamine, and then 62.8 mg of 1,3-bis(diphenylphosphino)propane and 34.2 mg of palladium(II) acetate were added. Under stirring at room temperature, a carbon monoxide gas was bubbled into the reaction solution for 5 minutes and the solution was further heated at reflux for one hour while bubbling the carbon monoxide gas. After air cooling, water and ethyl acetate were added to the reaction solution and insolubles were removed by filtration, and then the filtrate was extracted with ethyl acetate. The extract was washed with water and dried over anhydrous magnesium sulfate and the solvent was distilled off under reduced pressure. The residue was purified by silica gel column chromatography to obtain 392 mg of the objective compound as a pale yellow oily product.

$^1$H-NMR (CDCl$_3$) δ: 2.29 (3H, s), 2.39 (3H, s), 2.46 (8H, br), 3.49 (2H, s), 3.90 (3H, s), 7.36 (1H, d), 7.81 (1H, d), 7.83 (1H, s)

Step 6

3-methyl-4-(4-methylpiperazin-1-ylmethyl)benzoic acid dihydrochloride

In the same manner as in Reference Example 1 (step 4), except that methyl 3-methyl-4-(4-methylpiperazin-1-ylmethyl)benzoate obtained in the step 5 was used in place of ethyl 3-bromo-4-(4-methylpiperazin-1-ylmethyl)benzoate, the objective compound was prepared.

Colorless Crystal

Step 7

3-methyl-4-(4-methylpiperazin-1-ylmethyl)benzoyl chloride dihydrochloride

In the same manner as in Reference Example 1 (step 5), except that 3-methyl-4-(4-methylpiperazin-1-ylmethyl)benzoic acid dihydrochloride obtained in the step 6 was used in place of 3-bromo-4-(4-methylpiperazin-1-ylmethyl)benzoic acid dihydrochloride, the objective compound was prepared.

Colorless Crystal

REFERENCE EXAMPLE 20

4-(4-methylpiperazin-1-ylmethyl)-3-nitrobenzoyl chloride dihydrochloride

Step 1

Ethyl 4-(bromomethyl)-3-nitrobenzoate

In the same manner as in Reference Example 1 (step 1), except that 4-(bromomethyl)-3-nitrobenzoic acid was used in place of 3-bromo-4-methylbenzoic acid, the objective compound was prepared.

Yellow Oily Product $^1$H-NMR (CDCl$_3$) δ: 1.43 (3H, t), 4.48 (2H, q), 4.85 (2H, s), 7.67 (1H, d), 8.26 (1H, dd), 8.67 (1H, d)

Step 2

Ethyl 4-(4-methylpiperazin-1-ylmethyl)-3-nitrobenzoate

In the same manner as in Reference Example 1 (step 3), except that ethyl 4-(bromomethyl)-3-nitrobenzoate obtained in the step 1 was used in place of ethyl 3-bromo-4-(bromomethyl)benzoate, the objective compound was prepared.

Yellow Crystal

Melting point: 92-94° C. $^1$H-NMR (CDCl$_3$) δ: 1.42 (3H, t), 2.28 (3H, s), 2.33-2.54 (8H, br), 3.83 (2H, s), 4.42 (2H, q), 7.71 (1H, d), 8.19 (1H, dd), 8.45 (1H, d)

Step 3

4-(4-methylpiperazin-1-ylmethyl)-3-nitrobenzoic acid dihydrochloride

In the same manner as in Reference Example 1 (step 4), except that ethyl 4-(4-methylpiperazin-1-ylmethyl)-3-nitrobenzoate obtained in the step 2 was used in place of ethyl 3-bromo-4-(4-methylpiperazin-1-ylmethyl)benzoate, the objective compound was prepared.

Pale Brown Crystal

Melting point: 180° C. (with decomposition) $^1$H-NMR (D$_2$O) δ: 2.88 (3H, s), 3.30-3.90 (8H, br), 4.58 (2H, s), 7.72 (1H, d), 8.24 (1H, dd), 8.66 (1H, d)

Step 4

4-(4-methylpiperazin-1-ylmethyl)-3-nitrobenzoyl chloride dihydrochloride

In the same manner as in Reference Example 1 (step 5), except that 4-(4-methylpiperazin-1-ylmethyl)-3-nitrobenzoic acid dihydrochloride obtained in the step 3 was used in place of 3-bromo-4-(4-methylpiperazin-1-ylmethyl)benzoic acid dihydrochloride, the objective compound was prepared.

Pale Brown Crystal

Melting point: 190° C. (with decomposition) $^1$H-NMR (D$_2$O) δ: 2.99 (3H, s), 3.25-4.00 (8H, br), 4.66 (2H, s), 7.75 (1H, d), 8.28 (1H, d), 8.72 (1H, br)

REFERENCE EXAMPLE 21

3-methoxy-4-(4-methylpiperazin-1-ylmethyl)benzoyl chloride dihydrochloride

In the same manner as in Reference Example 1 (steps 2 to 5), except that methyl 3-methoxy-4-methylbenzoate was used in place of ethyl 3-bromo-4-methylbenzoate in the step 2, the objective compound was prepared.

Colorless Crystal $^1$H-NMR (D$_2$O) δ: 2.88 (3H, s), 3.54 (8H, br), 3.80 (3H, s), 4.41 (2H, s), 7.39 (1H, d), 7.52 (2H, m)

REFERENCE EXAMPLE 22

3,5-dibromo-4-(4-methylpiperazin-1-ylmethyl)benzoyl chloride dihydrochloride

In the same manner as in Reference Example 1 (steps 2 to 5), except that methyl 3,5-dibromo-4-methylbenzoate was used in place of ethyl 3-bromo-4-methylbenzoate in the step 2, the objective compound was prepared.

Pale Orange Crystal $^1$H-NMR (D$_2$O) δ: 2.89 (3H, s), 3.73 (8H, br), 4.73 (2H, s), 8.19 (2H, s)

REFERENCE EXAMPLE 23

3,5-dimethoxy-4-(4-methylpiperazin-1-ylmethyl)benzoyl chloride dihydrochloride

In the same manner as in Reference Example 1, except that 3,5-dimethoxy-4-methylbenzoic acid was used in place of 3-bromo-4-methylbenzoic acid in the step 1, the objective compound was prepared.

Pale Yellow Crystal $^1$H-NMR (D$_2$O) δ: 2.92 (3H, s), 3.58 (8H, br), 3.82 (6H, s), 4.44 (2H, s), 7.20 (2H, s)

REFERENCE EXAMPLE 24

3-(N,N-dimethylcarbamoyl)-4-(4-methylpiperazin-1-ylmethyl)benzoyl chloride dihydrochloride Step 1

Ethyl 3-(N,N-dimethylcarbamoyl)-4-methylbenzoate

This compound was prepared by version of the method described in the document (Org. Lett., 2002, 4, 2849-2851). 1.00 g of ethyl 3-iodo-4-methylbenzoate (intermediate of Reference Example 2) was dissolved in 30 ml of N,N-dimethylformamide and 23 mg of tris(dibenzylideneacetone)dipalladium(0) was added. Under stirring at room temperature, 643 µl of phosphorus oxychloride was added, followed by stirring with heating at 120° C. for 12 hours under an argon atmosphere. The reaction solution was mixed with an aqueous saturated sodium hydrogen carbonate solution, extracted twice with ethyl acetate, washed with saturated saline and dried over anhydrous magnesium sulfate, and then the solvent was distilled off under reduced pressure. The residue was purified by silica gel column chromatography to obtain 338 mg of the objective compound as a brown oily product.

$^1$H-NMR (CDCl$_3$) δ: 1.38 (3H, t), 2.35 (3H, s), 2.84 (3H, s), 3.15 (3H, s), 4.36 (2H, q), 7.29 (1H, d), 7.87 (1H, d), 7.95 (1H, dd)

Step 2

Ethyl 4-(bromomethyl)-3-(N,N-dimethylcarbamoyl)benzoate

In the same manner as in Reference Example 1 (step 2), except that ethyl 3-(N,N-dimethylcarbamoyl)-4-methylbenzoate obtained in the step 1 was used in place of ethyl 3-bromo-4-methylbenzoate, the objective compound was prepared.

Yellow Oily Product $^1$H-NMR (CDCl$_3$) δ: 1.38 (3H, t), 2.91 (3H, s), 3.18 (3H, s), 4.36 (2H, q), 4.60 (2H, s), 7.51 (1H, d), 7.88 (1H, d), 7.98 (1H, dd)

Step 3

Ethyl 3-(N,N-dimethylcarbamoyl)-4-(4-methylpiperazin-1-ylmethyl)benzoate

In the same manner as in Reference Example 1 (step 3), except that ethyl 4-(bromomethyl)-3-(N,N-dimethylcarbamoyl)benzoate obtained in the step 2 was used in place of ethyl 3-bromo-4-(bromomethyl)benzoate, the objective compound was prepared.

Brown Oily Product $^1$H-NMR (CDCl$_3$) δ: 1.39 (3H, t), 2.28 (3H, s), 2.46 (8H, br), 2.86 (3H, s), 3.13 (3H, s), 3.58 (2H, br), 4.37 (2H, q), 7.45 (1H, d), 7.86 (1H, d), 7.97 (1H, dd)

Step 4

3-(N,N-dimethylcarbamoyl)-4-(4-methylpiperazin-1-ylmethyl)benzoic acid dihydrochloride In the same manner as in Reference Example 1 (step 4), except that ethyl 3-(N,N-dimethylcarbamoyl)-4-(4-methylpiperazin-1-ylmethyl)benzoate obtained in the step 3 was used in place of ethyl 3-bromo-4-(4-methylpiperazin-1-ylmethyl)benzoate, the objective compound was prepared.

Pale Yellow Amorphous $^1$H-NMR (D$_2$O) δ: 2.83 (3H, s), 2.87 (3H, s), 3.02 (3H, s), 3.44 (8H, br), 4.28 (2H, s), 7.63 (1H, d), 7.97 (1H, d), 8.05 (1H, dd)

Step 5

3-(N,N-dimethylcarbamoyl)-4-(4-methylpiperazin-1-ylmethyl)benzoyl chloride dihydrochloride In the same manner as in Reference Example 1 (step 5), except that 3-(N,N-dimethylcarbamoyl)-4-(4-methylpiperazin-1-ylmethyl)benzoic acid dihydrochloride obtained in the step 4 was used in place of 3-bromo-4-(4-methylpiperazin-1-ylmethyl)benzoic acid dihydrochloride, the objective compound was prepared.

Pale Orange Crystal $^1$H-NMR (D$_2$O) δ: 2.83 (3H, s), 2.87 (3H, s), 3.03 (3H, s), 3.47 (8H, br), 4.29 (2H, s), 7.64 (1H, d), 7.99 (1H, d), 8.06 (1H, dd)

REFERENCE EXAMPLE 25

3-bromo-4-(4-ethylpiperazin-1-ylmethyl)benzoyl chloride dihydrochloride

In the same manner as in Reference Example 1, except that N-ethylpiperazine was used in place of N-methylpiperazine in the step 3, the objective compound was prepared.

Pale Brown Crystal $^1$H-NMR (D$_2$O) δ: 1.33 (3H, t), 3.34 (2H, q), 3.67 (8H, br), 4.73 (2H, s), 7.73 (1H, d), 8.03 (1H, dd), 8.32 (1H, d)

REFERENCE EXAMPLE 26

3-bromo-4-[4-(n-propyl)piperazin-1-ylmethyl]benzoyl chloride dihydrochloride

In the same manner as in Reference Example 1, except that N-(n-propyl)piperazine was used in place of N-methylpiperazine in the step 3, the objective compound was prepared.

Colorless Crystal $^1$H-NMR (D$_2$O) δ: 0.95 (3H, t), 1.75 (2H, m), 3.23 (2H, m), 3.79 (8H, br), 4.73 (2H, s), 7.73 (1H, d), 8.05 (1H, dd), 8.35 (1H, d)

REFERENCE EXAMPLE 27

3-bromo-4-(N,N-dimethylaminomethyl)benzoyl chloride dihydrochloride

In the same manner as in Reference Example 1, except that dimethylamine was used in place of N-methylpiperazine in the step 3, the objective compound was prepared.

Colorless Crystal $^1$H-NMR (D$_2$O) δ: 2.80 (6H, d), 4.41 (2H, s), 7.53 (1H, d), 7.88 (1H, dd), 8.16 (1H, d)

REFERENCE EXAMPLE 28

3-bromo-4-(N,N-diethylaminomethyl)benzoyl chloride dihydrochloride

In the same manner as in Reference Example 1, except that diethylamine was used in place of N-methylpiperazine in the step 3, the objective compound was prepared.

Colorless Crystal $^1$H-NMR (D$_2$O) δ: 1.34 (6H, t), 3.29 (4H, q), 4.52 (2H, s), 7.65 (1H, d), 7.99 (1H, dd), 8.26 (1H, d)

REFERENCE EXAMPLE 29

3-bromo-4-(1-pyrrolidinylmethyl)benzoyl chloride dihydrochloride

In the same manner as in Reference Example 1, except that pyrrolidine was used in place of N-methylpiperazine in the step 3, the objective compound was prepared.

Pale Brown Crystal $^1$H-NMR (D$_2$O) δ: 1.95 (4H, m), 3.16 (2H, m), 3.46 (2H, m), 4.47 (2H, s), 7.54 (1H, d), 7.88 (1H, d), 8.17 (1H, s)

REFERENCE EXAMPLE 30

3-bromo-4-(piperidinomethyl)benzoyl chloride dihydrochloride

In the same manner as in Reference Example 1, except that piperidine was used in place of N-methylpiperazine in the step 3, the objective compound was prepared.

Colorless Crystal $^1$H-NMR (D$_2$O) δ: 1.69 (6H, m), 3.14 (2H, t), 3.53 (2H, d), 4.50 (2H, s), 7.66 (1H, d), 8.00 (1H, d), 8.29 (1H, s)

REFERENCE EXAMPLE 31

3-bromo-4-(morpholinomethyl)benzoyl chloride dihydrochloride

In the same manner as in Reference Example 1, except that morpholine was used in place of N-methylpiperazine in the step 3, the objective compound was prepared.

Pink Crystal $^1$H-NMR (D$_2$O) δ: 3.39 (4H, m), 3.69 (2H, m), 3.99 (2H, m), 4.51 (2H, s), 7.60 (1H, d), 7.92 (1H, dd), 8.22 (1H, s)

REFERENCE EXAMPLE 32

3-bromo-4-(cis-3,5-dimethylpiperazin-1-ylmethyl) benzoic acid dihydrochloride

In the same manner as in Reference Example 1 (steps 1 to 4), except that cis-2,6-dimethylpiperazine was used in place of N-methylpiperazine in the step 3, the objective compound was prepared.

Colorless Crystal $^1$H-NMR (D$_2$O) δ: 1.25 (6H, d), 3.11 (2H, t), 3.62 (4H, m), 4.53 (2H, s), 4.73 (2H, s), 7.59 (1H, d), 7.90 (1H, dd), 8.20 (1H, d)

REFERENCE EXAMPLE 33

3-bromo-4-(4-methyl-hexahydro-1H-1,4-diazepin-1-ylmethyl)benzoic acid dihydrochloride In the same manner as in Reference Example 1 (steps 1 to 4), except that 4-methyl-hexahydro-1H-1,4-diazepine was used in place of N-methylpiperazine in the step 3, the objective compound was prepared.

Yellow Crystal $^1$H-NMR (D$_2$O) δ: 2.23 (2H, br), 2.88 (3H, s), 3.57 (4H, br), 3.74 (4H, s), 4.58 (2H, s), 7.61 (1H, d), 7.90 (1H, dd), 8.17 (1H, d)

REFERENCE EXAMPLE 34

3-bromo-4-[4-(t-butoxycarbonyl)piperazin-1-ylmethyl]benzoic acid

Step 1

Ethyl 3-bromo-4-[4-(t-butoxycarbonyl)piperazin-1-ylmethyl]benzoate 1.00 g of ethyl 3-bromo-4-(bromomethyl)benzoate (intermediate of Reference Example 1) was dissolved in 10 ml of anhydrous tetrahydrofuran and, after adding 473 mg of potassium carbonate, 467 mg of N-(t-butoxycarbonyl)piperazine was added dropwise while stirring at room temperature under an argon atmosphere. After stirring at room temperature for 20 hours, insolubles were removed by filtration and the solvent in the filtrate was distilled off under reduced pressure. The residue was purified by silica gel column chromatography to obtain 918 mg of the objective compound as a pale yellow oily product.

$^1$H-NMR (CDCl$_3$) δ: 1.40 (3H, t), 1.46 (9H, s), 2.47 (4H, t), 3.45 (4H, m), 3.63 (2H, s), 4.38 (2H, q), 7.58 (1H, d), 7.96 (1H, dd), 8.21 (1H, d)

Step 2

3-bromo-4-[4-(t-butoxycarbonyl)piperazin-1-ylmethyl]benzoic acid 898 mg of ethyl 3-bromo-4-[4-(t-butoxycarbonyl)piperazin-1-ylmethyl]benzoate obtained in the step 1 was dissolved in 5 ml of methanol and 3.2 ml of an aqueous 1N sodium hydroxide solution was added. After stirring at room temperature for 3 hours, the mixture was neutralized by slowly adding 3.2 ml of a 1N hydrochloric acid. The deposited crystal was collected by filtration, washed with water and then dried under reduced pressure to obtain 796 mg of the objective compound as a colorless crystal.

Melting point: 204-205° C. (with decomposition)
$^1$H-NMR (DMSO-d$_6$) δ: 1.40 (9H, s), 2.40 (4H, t), 3.36 (4H, m), 3.61 (2H, s), 7.63 (1H, d), 7.92 (1H, dd), 8.07 (1H, d)

REFERENCE EXAMPLE 35

4-[4-(t-butoxycarbonyl)piperazin-1-ylmethyl]-3-trifluoromethylbenzoic acid

In the same manner as in Reference Example 34, except that ethyl 4-(bromomethyl)-3-trifluoromethylbenzoate (intermediate of Reference Example 5) was used in place of ethyl 3-bromo-4-(bromomethyl)benzoate in the step 1, the objective compound was prepared.

Colorless Crystal

Melting point: 126-134° C. $^1$H-NMR (CDCl$_3$) δ: 1.47 (9H, s), 2.55 (4H, br), 3.54 (4H, br), 3.84 (2H, s), 8.05 (1H, d), 8.25 (1H, d), 8.37 (1H, s)

EXAMPLE 1

3-bromo-4-(4-methylpiperazin-1-ylmethyl)-N-{4-methyl-3-[4-(3-pyridyl)pyrimidin-2-ylamino]phenyl}benzamide 0.74 g of 4-methyl-3-[4-(3-pyridyl)pyrimidin-2-ylamino] aniline (Japanese Unexamined Patent Publication (Kokai) No. 6-87834) was dissolved in 27 ml of anhydrous pyridine and 920 mg of 3-bromo-4-(4-methylpiperazin-1-ylmethyl) benzoyl chloride dihydrochloride (Reference Example 1) was added, followed by stirring at room temperature for 14 hours. The reaction solution was mixed with ice water and aqueous saturated sodium hydrogen carbonate solution and then extracted with ethyl acetate. The extract was washed with water and dried over anhydrous magnesium sulfate, and then the solvent was distilled off under reduced pressure. The residue was purified by silica gel column chromatography to obtain 1.48 g of a crude product. The crude product was crystallized by adding chloroform-diethyl ether (1:1) and the crystal was collected by filtration to obtain 1.05 g of the objective compound as a colorless crystal.

Melting point: 202-203° C. (with decomposition) Elemental analysis (for C$_{29}$H$_{30}$BrN$_7$O.0.9H$_2$O) Calcd. (%): C, 59.17; H, 5.44; N, 16.65. Found (%): C, 59.16; H, 5.21; N, 16.64

EXAMPLE 2

3-iodo-4-(4-methylpiperazin-1-ylmethyl)-N-{4-methyl-3-[4-(3-pyridyl)pyrimidin-2-ylamino]phenyl}benzamide This compound was prepared in the same manner as in Example 1, except that 3-iodo-4-(4-methylpiperazin-1-ylmethyl)benzoyl chloride dihydrochloride (Reference Example 2) was used in place of 3-bromo-4-(4-methylpiperazin-1-ylmethyl)benzoyl chloride dihydrochloride, and that the reaction was conducted at room temperature for 24 hours and the resulting crystal was recrystallized from methanol.

Colorless Crystal

Melting point: 199-200° C. (with decomposition) Elemental analysis (for C$_{29}$H$_{30}$IN$_7$O) Calcd. (%): C, 56.23; H, 4.88; N, 15.83. Found (%): C, 56.13; H, 4.94; N, 15.80

EXAMPLE 3

3-chloro-4-(4-methylpiperazin-1-ylmethyl)-N-{4-methyl-3-[4-(3-pyridyl)pyrimidin-2-ylamino]phenyl}benzamide This compound was prepared in the same manner as in Example 1, except that 3-chloro-4-(4-methylpiperazin-1-ylmethyl)benzoyl chloride dihydrochloride (Reference Example 3) was used in place of 3-bromo-4-(4-methylpiperazin-1-ylmethyl)benzoyl chloride dihydrochloride, and that the reaction was conducted at room temperature for 24 hours.

Colorless Crystal

Melting point: 193-194° C. (with decomposition) Elemental analysis (for C$_{29}$H$_{30}$ClN$_7$O.0.6H$_2$O) Calcd. (%): C, 64.64; H, 5.84; N, 18.20. Found (%): C, 64.62; H, 5.60; N, 18.23

EXAMPLE 4

3-fluoro-4-(4-methylpiperazin-1-ylmethyl)-N-{4-methyl-3-[4-(3-pyridyl)pyrimidin-2-ylamino]phenyl}benzamide This compound was prepared in the same manner as in Example 1, except that 3-fluoro-4-(4-methylpiperazin-1-ylmethyl)benzoyl chloride dihydrochloride (Reference Example 4) was used in place of 3-bromo-4-(4-methylpiperazin-1-ylmethyl)benzoyl chloride dihydrochloride, and that the reaction was conducted at room temperature for 22 hours and the crude crystal obtained by purification with silica gel column chromatography was washed with chloroform-diethyl ether (1:1).

Colorless Crystal

Melting point: 197-199° C. (with decomposition) Elemental analysis (for C$_{29}$H$_{30}$FN$_7$O.0.3H$_2$O) Calcd. (%): C, 67.37; H, 5.97; N, 18.96. Found (%): C, 67.36; H, 5.96; N, 18.93

EXAMPLE 5

4-(4-methylpiperazin-1-ylmethyl)-3-trifluoromethyl-N-{4-methyl-3-[4-(3-pyridyl)pyrimidin-2-ylamino]phenyl}benzamide This compound was prepared in the same manner as in Example 1, except that 4-(4-methylpiperazin-1-ylmethyl)-3-trifluoromethylbenzoyl chloride dihydrochloride (Reference Example 5) was used in place of 3-bromo-4-(4-methylpiperazin-1-ylmethyl)benzoyl chloride dihydrochloride, that the reaction was conducted at room temperature for 22 hours and the resulting crystal was washed with diethyl ether.
Colorless Crystal
Melting point: 182-183° C. (with decomposition) Elemental analysis (for $C_{30}H_{30}F_3N_7O\cdot 0.3H_2O$) Calcd. (%): C, 63.55; H, 5.44; N, 17.29. Found (%): C, 63.43; H, 5.37; N, 17.29

EXAMPLE 6

4-(4-methylpiperazin-1-ylmethyl)-3-trifluoromethyl-N-{4-methyl-3-[4-(5-pyrimidinyl)pyrimidin-2-ylamino]phenyl}benzamide This compound was prepared in the same manner as in Example 1, except that 4-(4-methylpiperazin-1-ylmethyl)-3-trifluoromethylbenzoyl chloride dihydrochloride (Reference Example 5) was used in place of 3-bromo-4-(4-methylpiperazin-1-ylmethyl)benzoyl chloride dihydrochloride and 4-methyl-3-[4-(5-pyrimidinyl)pyrimidin-2-ylamino]aniline (Reference Example 6) was used in place of 4-methyl-3-[4-(3-pyridinyl)pyrimidin-2-ylamino]aniline, and that the reaction was conducted at room temperature for 20 hours and the crude crystal obtained by purification with silica gel column chromatography was washed with diethyl ether.
Pale Yellow Crystal
Melting point: 231-233° C. (with decomposition) Elemental analysis (for $C_{29}H_{29}F_3N_8O\cdot 0.2H_2O$) Calcd. (%): C, 61.52; H, 5.23; N, 19.79. Found (%): C, 61.37; H, 5.24; N, 19.81

EXAMPLE 7

3-bromo-4-(4-methylpiperazin-1-ylmethyl)-N-{4-methyl-3-[4-(2-pyrazinyl)pyrimidin-2-ylamino]phenyl}benzamide This compound was prepared in the same manner as in Example 1, except that 4-methyl-3-[4-(2-pyrazinyl)pyrimidin-2-ylamino]aniline (Reference Example 7) was used in place of 4-methyl-3-[4-(3-pyridinyl)pyrimidin-2-ylamino]aniline, and that the reaction was conducted at room temperature for 18 hours.
Pale Yellow Crystal
Melting point: 213-214° C. (with decomposition) Elemental analysis (for $C_{28}H_{29}BrN_8O$) Calcd. (%): C, 58.64; H, 5.10; N, 19.54. Found (%): C, 58.41; H, 5.11; N, 19.24

EXAMPLE 8

3-bromo-4-(4-methylpiperazin-1-ylmethyl)-N-{3-[4-(6-chloropyridin-3-yl)pyrimidin-2-ylamino]-4-methylphenyl}benzamide 629 mg of 3-[4-(6-chloropyridin-3-yl)pyrimidin-2-ylamino]-4-methylaniline (Reference Example 8) was suspended in 7 ml of acetonitrile, and then 24 mg of 4-dimethylaminopyridine and 1.15 ml of N,N-diisopropyl-N-ethylamine were added in turn. Under ice-cool stirring, 979 mg of 3-bromo-4-(4-methylpiperazin-1-ylmethyl)benzoyl chloride dihydrochloride (Reference Example 1) was added by five portions, followed by stirring at room temperature for one hour after removing an ice bath. The reaction solution was mixed with water, extracted with chloroform and then dried over anhydrous magnesium sulfate. The solvent was distilled off under reduced pressure and the residue was purified by silica gel column chromatography. The resulting crude crystal was washed in turn with ethyl acetate and diethyl ether and the crystal was collected by filtration to obtain 939 mg of the objective compound as a pale yellow crystal.
Melting point: 219-222° C. (with decomposition) Elemental analysis (for $C_{29}H_{29}BrClN_7O$) Calcd. (%): C, 57.39; H, 4.82; N, 16.15. Found (%): C, 57.07; H, 4.75; N, 16.09

EXAMPLE 9

3-bromo-4-(4-methylpiperazin-1-ylmethyl)-N-{3-[4-(5-bromopyridin-3-yl)pyrimidin-2-ylamino]-4-methylphenyl}benzamide This compound was prepared in the same manner as in Example 8, except that 3-[4-(5-bromopyridin-3-yl)pyrimidin-2-ylamino]-4-methylaniline (Reference Example 9) was used in place of 3-[4-(6-chloropyridin-3-yl)pyrimidin-2-ylamino]-4-methylaniline, and that the crude crystal obtained by purification with silica gel column chromatography was recrystallized from ethyl acetate-diethyl ether.
Pale Yellow Crystal
Melting point: 194-195° C. (with decomposition) Elemental analysis (for $C_{29}H_{29}Br_2N_7O\cdot 0.3H_2O$) Calcd. (%): C, 53.03; H, 4.54; N, 14.93. Found (%): C, 53.07; H, 4.53; N, 14.70

EXAMPLE 10

4-(4-methylpiperazin-1-ylmethyl)-3-trifluoromethyl-N-{3-[4-(5-bromopyridin-3-yl)pyrimidin-2-ylamino]-4-methylphenyl}benzamide This compound was prepared in the same manner as in Example 8, except that 3-[4-(5-bromopyridin-3-yl)pyrimidin-2-ylamino]-4-methylaniline (Reference Example 9) was used in place of 3-[4-(6-chloropyridin-3-yl)pyrimidin-2-ylamino]-4-methylaniline and 4-(4-methylpiperazin-1-ylmethyl)-3-trifluoromethylbenzoyl chloride dihydrochloride (Reference Example 5) was used in place of 3-bromo-4-(4-methylpiperazin-1-ylmethyl)benzoyl chloride dihydrochloride, and that the oily product purified by silica gel column chromatography was crystallized by adding diisopropyl ether-ethyl acetate.
Pale Yellow Crystal
Melting point: 171-173° C. (with decomposition) Elemental analysis (for $C_{30}H_{29}BrF_3N_7O\cdot 0.7H_2O$) Calcd. (%): C, 55.17; H, 4.69; N, 15.01. Found (%): C, 55.16; H, 4.57; N, 14.94

EXAMPLE 11

3-bromo-4-(4-methylpiperazin-1-ylmethyl)-N-{3-[4-(1,2-dihydropyridazin-4-yl)pyrimidin-2-ylamino]-4-methylphenyl}benzamide This compound was prepared in the same manner as in Example 8, except that 3-[4-(1,2-dihydropyridazin-4-yl)pyrimidin-2-ylamino]-4-methylaniline (Reference Example 10) was used in place of 3-[4-(6-chloropyridin-3-yl)pyrimidin-2-ylamino]-4-methylaniline, and that extraction was conducted with ethyl acetate and the residue obtained by purification with silica gel column chromatography was washed with diisopropyl ether.
Pale Yellow Amorphous
Elemental analysis (for $C_{28}H_{31}BrN_8O.0.8\{(CH_3)_2CH\}_2O$) Calcd. (%): C, 59.94; H, 6.47; N, 17.05. Found (%): C, 59.51; H, 6.30; N, 16.80

EXAMPLE 12

3-bromo-4-(4-methylpiperazin-1-ylmethyl)-N-{4-methyl-3-[4-(3-pyridazinyl)pyrimidin-2-ylamino]phenyl}benzamide This compound was prepared in the same manner as in Example 8, except that 4-methyl-3-[4-(3-pyridazinyl)pyrimidin-2-ylamino]aniline (Reference Example 11) was used in place of 3-[4-(6-chloropyridin-3-yl)pyrimidin-2-ylamino]-4-methylaniline, and that the crude crystal obtained by purification with silica gel column chromatography was washed with ethyl acetate-chloroform.
Pale Yellow Crystal
Melting point: 185-187° C. (with decomposition) Elemental analysis (for $C_{28}H_{29}BrN_8O.0.1H_2O$) Calcd. (%): C, 58.28; H, 5.13; N, 19.42. Found (%): C, 58.24; H, 5.00; N, 19.48

EXAMPLE 13

3-bromo-4-(4-methylpiperazin-1-ylmethyl)-N-{4-methyl-3-[4-(5-pyrimidinyl)pyrimidin-2-ylamino]phenyl}benzamide 150 mg of 4-methyl-3-[4-(5-pyrimidinyl)pyrimidin-2-ylamino]aniline (Reference Example 6) was dissolved in 4 ml of N,N-dimethylformamide, and then 255 mg of 3-bromo-4-(4-methylpiperazin-1-ylmethyl)benzoic acid dihydrochloride (Reference Example 1) and 109 mg of triethylamine were added in turn. While stirring the suspension at room temperature, 106 mg of diethyl cyanophosphonate and 55 mg of triethylamine were added in turn, followed by stirring at room temperature for 3 hours. After the solvent was distilled off under reduced pressure, the residue was mixed with water and an aqueous saturated sodium hydrogen carbonate solution and then extracted with chloroform. The extract was washed with water and dried over anhydrous magnesium sulfate, and then the solvent was distilled off under reduced pressure. The residue was purified by silica gel column chromatography to obtain 240 mg of a crude product. The crude product was dissolved in chloroform-methanol and 2-propanol was added, followed by concentration under reduced pressure. The deposited crystal was collected by filtration and washed in turn with 2-propanol and diethyl ether to obtain 147 mg of the objective compound as a pale yellow crystal.
Melting point: 238-240° C. (with decomposition) Elemental analysis (for $C_{28}H_{29}BrN_8O.0.1H_2O$) Calcd. (%): C, 58.46; H, 5.12; N, 19.48. Found (%): C, 58.21; H, 5.02; N, 19.30

EXAMPLE 14

3-bromo-4-(4-methylpiperazin-1-ylmethyl)-N-{4-methyl-3-[4-(3-pyridyl)pyridin-2-ylamino]phenyl}benzamide This compound was prepared in the same manner as in Example 8, except that 4-methyl-3-[4-(3-pyridyl)pyridin-2-ylamino]aniline (Reference Example 12) was used in place of 3-[4-(6-chloropyridin-3-yl)pyrimidin-2-ylamino]-4-methylaniline, and that the crude crystal obtained by purification with silica gel column chromatography was washed with ethyl acetate-chloroform-methanol.
Pale Yellow Crystal
Melting point: 244-245° C. (with decomposition) Elemental analysis (for $C_{30}H_{31}BrN_6O.0.6H_2O$) Calcd. (%): C, 61.88; H, 5.57; N, 14.43. Found (%): C, 61.71; H, 5.49; N, 14.13

EXAMPLE 15

3-bromo-4-(4-methylpiperazin-1-ylmethyl)-N-{4-methyl-3-[4-(5-pyrimidinyl)pyridin-2-ylamino]phenyl}benzamide This compound was prepared in the same manner as in Example 8, except that 4-methyl-3-[4-(5-pyrimidinyl)pyridin-2-ylamino]aniline (Reference Example 13) was used in place of 3-[4-(6-chloropyridin-3-yl)pyrimidin-2-ylamino]-4-methylaniline, and that the crude crystal obtained by purification with silica gel column chromatography was washed with ethyl acetate-diethyl ether.
Pale Yellow Crystal
Melting point: 244-246° C. (with decomposition) Elemental analysis (for $C_{29}H_{30}BrN_7O.0.2H_2O.0.2CH_3COOC_2H_5$) Calcd. (%): C, 60.28; H, 5.43; N, 16.51. Found (%): C, 60.12; H, 5.40; N, 16.28

EXAMPLE 16

3-bromo-4-(4-methylpiperazin-1-ylmethyl)-N-{4-methyl-3-[2-(3-pyridyl)pyridin-6-ylamino]phenyl}benzamide This compound was prepared in the same manner as in Example 8, except that 4-methyl-3-[2-(3-pyridyl)pyridin-6-ylamino]aniline (Reference Example 14) was used in place of 3-[4-(6-chloropyridin-3-yl)pyrimidin-2-ylamino]-4-methylaniline, and that the crude product purified by silica gel column chromatography was not further washed.
Pale Yellow Amorphous
Elemental analysis (for $C_{30}H_{31}BrN_6O.1.5H_2O$) Calcd. (%): C, 60.20; H, 5.73; N, 14.04 Found (%): C, 60.39; H, 5.55; N, 13.00. FAB-MS (Pos.) m/z 571, (Neg.) m/z 569

EXAMPLE 17

3-bromo-4-(4-methylpiperazin-1-ylmethyl)-N-{4-methyl-3-[3-(3-pyridyl)pyridin-5-ylamino]phenyl}benzamide This compound was prepared in the same manner as in Example 8, except that 4-methyl-3-[3-(3-pyridyl)pyridin-5-ylamino]aniline (Reference Example 15) was used in place of 3-[4-(6-chloropyridin-3-yl)pyrimidin-2-ylamino]-4-methylaniline, and that extraction was conducted with ethyl acetate and the oily product purified by silica gel column chromatography was crystallized by adding ethyl acetate-diethyl ether.
Pale Yellow Crystal
Melting point: 139-141° C. Elemental analysis (for $C_{30}H_{31}BrN_6O.1.2H_2O$) Calcd. (%): C, 60.75; H, 5.68; N, 14.17. Found (%): C, 60.96; H, 5.62; N, 13.98

EXAMPLE 18

3-bromo-4-(4-methylpiperazin-1-ylmethyl)-N-{4-methyl-3-[3-(3-pyridyl)phenylamino]phenyl}benzamide This compound was prepared in the same manner as in Example 8, except that 4-methyl-3-[3-(3-pyridyl)phenylamino]aniline (Reference Example 16) was used in place of 3-[4-(6-chloropyridin-3-yl)pyrimidin-2-ylamino]-4-methylaniline, and that extraction was conducted with ethyl acetate and the oily product purified by silica gel column chromatography was crystallized by adding ethyl acetate-hexane.

Pale Brown Crystal

Melting point: 174-175° C. Elemental analysis (for $C_{31}H_{32}BrN_5O$) Calcd. (%): C, 65.26; H, 5.65; N, 12.28. Found (%): C, 65.12; H, 5.73; N, 12.19

EXAMPLE 19

3-bromo-4-(4-methylpiperazin-1-ylmethyl)-N-{4-methyl-3-[2-(3-pyridyl)pyrazin-6-ylamino]phenyl}benzamide This compound was prepared in the same manner as in Example 8, except that 4-methyl-3-[2-(3-pyridyl)pyrazin-6-ylamino]aniline (Reference Example 17) was used in place of 3-[4-(6-chloropyridin-3-yl)pyrimidin-2-ylamino]-4-methylaniline, and that extraction was conducted with ethyl acetate and the amorphous purified by silica gel column chromatography was crystallized by adding ethyl acetate.

Yellow Crystal

Melting point: 192-193° C. Elemental analysis (for $C_{29}H_{30}BrN_7O \cdot 0.25H_2O$) Calcd. (%): C, 60.37; H, 5.33; N, 16.99. Found (%): C, 60.58; H, 5.35; N, 16.76

EXAMPLE 20

3-bromo-4-(4-methylpiperazin-1-ylmethyl)-N-{4-methyl-3-[5-(3-pyridyl)-1,2,4-triazin-3-ylamino]phenyl}benzamide This compound was prepared in the same manner as in Example 8, except that 4-methyl-3-[5-(3-pyridyl)-1,2,4-triazin-3-ylamino]aniline (Reference Example 18) was used in place of 3-[4-(6-chloropyridin-3-yl)pyrimidin-2-ylamino]-4-methylaniline, and that the amorphous purified by silica gel column chromatography was crystallized by adding 2-propanol.

Yellow Crystal

Melting point: 219-221° C. Elemental analysis (for $C_{28}H_{29}BrN_8O \cdot 1.2H_2O \cdot 0.1CH_3CH(OH)CH_3$) Calcd. (%): C, 56.55; H, 5.40; N, 18.64. Found (%): C, 56.58; H, 5.00; N, 18.27

EXAMPLE 21

3-methyl-4-(4-methylpiperazin-1-ylmethyl)-N-{4-methyl-3-[4-(3-pyridyl)pyrimidin-2-ylamino]phenyl}benzamide This compound was prepared in the same manner as in Example 8, except that 4-methyl-3-[4-(3-pyridyl)pyrimidin-2-ylamino]aniline (Japanese Unexamined Patent Publication (Kokai) No. 6-87834) was used in place of 3-[4-(6-chloropyridin-3-yl)pyrimidin-2-ylamino]-4-methylaniline and 3-methyl-4-(4-methylpiperazin-1-ylmethyl)benzoyl chloride dihydrochloride (Reference Example 19) was used in place of 3-bromo-4-(4-methylpiperazin-1-ylmethyl)benzoyl chloride dihydrochloride, and that the oily product purified by silica gel column chromatography was crystallized by adding ethyl acetate.

Pale Yellow Crystal

Melting point: 192-193° C. Elemental analysis (for $C_{30}H_{33}N_7O$) Calcd. (%): C, 70.98; H, 6.55; N, 19.31. Found (%): C, 70.79; H, 6.67; N, 19.39

EXAMPLE 22

4-(4-methylpiperazin-1-ylmethyl)-3-nitro-N-{4-methyl-3-[4-(3-pyridyl)pyrimidin-2-ylamino]phenyl}benzamide This compound was prepared in the same manner as in Example 8, except that 4-methyl-3-[4-(3-pyridyl)pyrimidin-2-ylamino]aniline (Japanese Unexamined Patent Publication (Kokai) No. 6-87834) was used in place of 3-[4-(6-chloropyridin-3-yl)pyrimidin-2-ylamino]-4-methylaniline and 4-(4-methylpiperazin-1-ylmethyl)-3-nitrobenzoyl chloride dihydrochloride (Reference Example 20) was used in place of 3-bromo-4-(4-methylpiperazin-1-ylmethyl)benzoyl chloride dihydrochloride, and that extraction was conducted with ethyl acetate and the oily product purified by silica gel column chromatography was crystallized by adding ethyl acetate-diethyl ether.

Pale Yellow Crystal

Melting point: 184-186° C. Elemental analysis (for $C_{29}H_{30}N_8O_3 \cdot 0.7H_2O$) Calcd. (%): C, 63.19; H, 5.74; N, 20.33. Found (%): C, 63.38; H, 5.57; N, 20.00

EXAMPLE 23

3-methoxy-4-(4-methylpiperazin-1-ylmethyl)-N-{4-methyl-3-[4-(3-pyridyl)pyrimidin-2-ylamino]phenyl}benzamide This compound was prepared in the same manner as in Example 8, except that 4-methyl-3-[4-(3-pyridyl)pyrimidin-2-ylamino]aniline (Japanese Unexamined Patent Publication (Kokai) No. 6-87834) was used in place of 3-[4-(6-chloropyridin-3-yl)pyrimidin-2-ylamino]-4-methylaniline and 3-methoxy-4-(4-methylpiperazin-1-ylmethyl)benzoyl chloride dihydrochloride (Reference Example 21) was used in place of 3-bromo-4-(4-methylpiperazin-1-ylmethyl)benzoyl chloride dihydrochloride, and that the oily product purified by silica gel column chromatography was crystallized by adding ethyl acetate and then washed with diethyl ether.

Pale Yellow Crystal

Melting point: 171-172° C. (with decomposition) Elemental analysis (for $C_{30}H_{33}N_7O_2 \cdot 0.6H_2O$) Calcd. (%): C, 67.42; H, 6.45; N, 18.35. Found (%): C, 67.23; H, 6.36; N, 18.19

EXAMPLE 24

3,5-dibromo-4-(4-methylpiperazin-1-ylmethyl)-N-{4-methyl-3-[4-(3-pyridyl)pyrimidin-2-ylamino]phenyl}benzamide This compound was prepared in the same manner as in Example 8, except that 4-methyl-3-[4-(3-pyridyl)pyrimidin-2-ylamino]aniline (Japanese Unexamined Patent Publication (Kokai) No. 6-87834) was used in place of 3-[4-(6-chloropyridin-3-yl)pyrimidin-2-ylamino]-4-methylaniline and 3,5-dibromo-4-(4-methylpiperazin-1-ylmethyl)benzoyl chloride dihydrochloride (Reference Example 22) was used in place of 3-bromo-4-(4-methylpiperazin-1-ylmethyl)benzoyl chloride dihydrochloride, and that the oily product purified by silica gel column chromatography was crystallized by adding ethyl acetate and then washed with diethyl ether.

Pale Yellow Crystal

Melting point: 227-229° C. Elemental analysis (for $C_{29}H_{29}Br_2N_7O.0.1H_2O.0.35CH_3CO_2C_2H_5$) Calcd. (%): C, 53.38; H, 4.72; N, 14.33. Found (%): C, 53.02; H, 4.74; N, 14.09

EXAMPLE 25

3,5-dimethoxy-4-(4-methylpiperazin-1-ylmethyl)-N-{4-methyl-3-[4-(3-pyridyl)pyrimidin-2-ylamino]phenyl}benzamide This compound was prepared in the same manner as in Example 8, except that 4-methyl-3-[4-(3-pyridyl)pyrimidin-2-ylamino]aniline (Japanese Unexamined Patent Publication (Kokai) No. 6-87834) was used in place of 3-[4-(6-chloropyridin-3-yl)pyrimidin-2-ylamino]-4-methylaniline and 3,5-dimethoxy-4-(4-methylpiperazin-1-ylmethyl)benzoyl chloride dihydrochloride (Reference Example 23) was used in place of 3-bromo-4-(4-methylpiperazin-1-ylmethyl)benzoyl chloride dihydrochloride, and that the oily product purified by silica gel column chromatography was crystallized by adding ethyl acetate.

Yellow Crystal

Melting point: 201-214° C. (with decomposition) Elemental analysis (for $C_{31}H_{35}N_7O_3.0.5H_2O$) Calcd. (%): C, 66.17; H, 6.45; N, 17.43 Found (%): C, 65.91; H, 6.42; N, 17.42

EXAMPLE 26

3-(N,N-dimethylcarbamoyl)-4-(4-methylpiperazin-1-ylmethyl)-N-{4-methyl-3-[4-(3-pyridyl)pyrimidin-2-ylamino]phenyl}benzamide This compound was prepared in the same manner as in Example 1, except that 3-(N,N-dimethylcarbamoyl)-4-(4-methylpiperazin-1-ylmethyl)benzoyl chloride dihydrochloride (Reference Example 24) was used in place of 3-bromo-4-(4-methylpiperazin-1-ylmethyl)benzoyl chloride dihydrochloride, and that the oily product purified by silica gel column chromatography was crystallized by adding ethyl acetate.

Orange Crystal

Melting point: 210-214° C. (with decomposition) Elemental analysis (for $C_{32}H_{36}N_8O_2.0.6H_2O$) Calcd. (%): C, 66.79; H, 6.52; N, 19.47. Found (%): C, 66.41; H, 6.17; N, 19.36

EXAMPLE 27

3-bromo-4-(4-ethylpiperazin-1-ylmethyl)-N-{4-methyl-3-[4-(3-pyridyl)pyrimidin-2-ylamino]phenyl}benzamide This compound was prepared in the same manner as in Example 8, except that 4-methyl-3-[4-(3-pyridyl)pyrimidin-2-ylamino]aniline (Japanese Unexamined Patent Publication (Kokai) No. 6-87834) was used in place of 3-[4-(6-chloropyridin-3-yl)pyrimidin-2-ylamino]-4-methylaniline and 3-bromo-4-(4-ethylpiperazin-1-ylmethyl)benzoyl chloride dihydrochloride (Reference Example 25) was used in place of 3-bromo.-4-(4-methylpiperazin-1-ylmethyl)benzoyl chloride dihydrochloride, and that the oily product purified by silica gel column chromatography was crystallized by adding ethyl acetate.

Pale Yellow Crystal

Melting point: 202-203° C. Elemental analysis (for $C_{30}H_{32}BrN_7O.0.25H_2O$) Calcd. (%): C, 60.97; H, 5.54; N, 16.59. Found (%): C, 60.96; H, 5.54; N, 16.32

EXAMPLE 28

3-bromo-4-[4-(n-propyl)piperazin-1-ylmethyl]-N-{4-methyl-3-[4-(3-pyridyl)pyrimidin-2-ylamino]phenyl}benzamide This compound was prepared in the same manner as in Example 8, except that 4-methyl-3-[4-(3-pyridyl)pyrimidin-2-ylamino]aniline (Japanese Unexamined Patent Publication (Kokai) No. 6-87834) was used in place of 3-[4-(6-chloropyridin-3-yl)pyrimidin-2-ylamino]-4-methylaniline and 3-bromo-4-[4-(n-propyl)piperazin-1-ylmethyl]benzoyl chloride dihydrochloride (Reference Example 26) was used in place of 3-bromo-4-(4-methylpiperazin-1-ylmethyl)benzoyl chloride dihydrochloride, and that the oily product purified by silica gel column chromatography was crystallized by adding ethyl acetate.

Pale Yellow Crystal

Melting point: 204-205° C. Elemental analysis (for $C_{31}H_{34}BrN_7O.0.4H_2O$) Calcd. (%): C, 61.26; H, 5.77; N, 16.13. Found (%): C, 61.48; H, 5.66; N, 15.79

EXAMPLE 29

3-bromo-4-(N,N-dimethylaminomethyl)-N-{4-methyl-3-[4-(3-pyridyl)pyrimidin-2-ylamino]phenyl}benzamide This compound was prepared in the same manner as in Example 8, except that 4-methyl-3-[4-(3-pyridyl)pyrimidin-2-ylamino]aniline (Japanese Unexamined Patent Publication (Kokai) No. 6-87834) was used in place of 3-[4-(6-chloropyridin-3-yl)pyrimidin-2-ylamino]-4-methylaniline and 3-bromo-4-(N,N-dimethylaminomethyl)benzoyl chloride dihydrochloride (Reference Example 27) was used in place of 3-bromo-4-(4-methylpiperazin-1-ylmethyl)benzoyl chloride dihydrochloride, and that the oily product purified by silica gel column chromatography was crystallized by adding ethyl acetate.

Colorless Crystal

Melting point: 154-155° C. Elemental analysis (for $C_{26}H_{25}BrN_6O$) Calcd. (%): C, 60.35; H, 4.87; N, 16.24. Found. (%): C, 60.20; H, 4.97; N, 16.13

EXAMPLE 30

3-bromo-4-(N,N-diethylaminomethyl)-N-{4-methyl-3-[4-(3-pyridyl)pyrimidin-2-ylamino]phenyl}benzamide This compound was prepared in the same manner as in Example 8, except that 4-methyl-3-[4-(3-pyridyl)pyrimidin-2-ylamino]aniline (Japanese Unexamined Patent Publication (Kokai) No. 6-87834) was used in place of 3-[4-(6-chloropyridin-3-yl)pyrimidin-2-ylamino]-4-methylaniline and 3-bromo-4-(N,N-diethylaminomethyl)benzoyl chloride dihydrochloride (Reference Example 28) was used in place of 3-bromo-4-(4-methylpiperazin-1-ylmethyl)benzoyl chloride dihydrochloride, and that the oily product purified by silica gel column chromatography was crystallized by adding ethyl acetate.

Pale Yellow Crystal

Melting point: 172-173° C. Elemental analysis (for $C_{28}H_{29}BrN_6O$) Calcd. (%): C, 61.65; H, 5.36; N, 15.41. Found (%): C, 61.35; H, 5.36; N, 15.35

EXAMPLE 31

3-bromo-4-(1-pyrrolidinylmethyl)-N-{4-methyl-3-[4-(3-pyridyl)pyrimidin-2-ylamino]phenyl}benzamide This compound was prepared in the same manner as in Example 8, except that 4-methyl-3-[4-(3-pyridyl)pyrimidin-2-ylamino]aniline (Japanese Unexamined Patent Publication (Kokai) No. 6-87834) was used in place of 3-[4-(6-chloropyridin-3-yl)pyrimidin-2-ylamino]-4-methylaniline and 3-bromo-4-(1-pyrrolidinylmethyl)benzoyl chloride dihydrochloride (Reference Example 29) was used in place of 3-bromo-4-(4-methylpiperazin-1-ylmethyl)benzoyl chloride dihydrochloride, and that the oily product purified by silica gel column chromatography was crystallized by adding ethyl acetate.

Pale Yellow Crystal

Melting point: 195-196° C. Elemental analysis (for $C_{28}H_{27}BrN_6O$) Calcd. (%): C, 61.88; H, 5.01; N, 15.46. Found (%): C, 61.68; H, 5.12; N, 15.11

EXAMPLE 32

3-bromo-4-(piperidinomethyl)-N-{4-methyl-3-[4-(3-pyridyl)pyrimidin-2-ylamino]phenyl}benzamide This compound was prepared in the same manner as in Example 8, except that 4-methyl-3-[4-(3-pyridyl)pyrimidin-2-ylamino]aniline (Japanese Unexamined Patent Publication (Kokai) No. 6-87834) was used in place of 3-[4-(6-chloropyridin-3-yl)pyrimidin-2-ylamino]-4-methylaniline and 3-bromo-4-(piperidinomethyl)benzoyl chloride dihydrochloride (Reference Example 30) was used in place of 3-bromo-4-(4-methylpiperazin-1-ylmethyl)benzoyl chloride dihydrochloride, and that the oily product purified by silica gel column chromatography was crystallized by adding ethyl acetate.

Pale Yellow Crystal

Melting point: 158-159° C. Elemental analysis (for $C_{29}H_{29}BrN_6O$) Calcd. (%): C, 62.48; H, 5.24; N, 15.07. Found (%): C, 62.23; H, 5.25; N, 14.83

EXAMPLE 33

3-bromo-4-(morpholinomethyl)-N-{4-methyl-3-[4-(3-pyridyl)pyrimidin-2-ylamino]phenyl}benzamide This compound was prepared in the same manner as in Example 8, except that 4-methyl-3-[4-(3-pyridyl)pyrimidin-2-ylamino]aniline (Japanese Unexamined Patent Publication (Kokai) No. 6-87834) was used in place of 3-[4-(6-chloropyridin-3-yl)pyrimidin-2-ylamino]-4-methylaniline and 3-bromo-4-(morpholinomethyl)benzoyl chloride dihydrochloride (Reference Example 31) was used in place of 3-bromo-4-(4-methylpiperazin-1-ylmethyl)benzoyl chloride dihydrochloride, and that the oily product purified by silica gel column chromatography was crystallized by adding ethyl acetate.

Pale Yellow Crystal

Melting point: 179-180° C. Elemental analysis (for $C_{28}H_{29}BrN_6O_2$) Calcd. (%): C, 60.11; H, 4.86; N, 15.02. Found (%): C, 59.94; H, 4.93; N, 14.96

EXAMPLE 34

3-bromo-4-(cis-3,5-dimethylpiperazin-1-ylmethyl)-N-{4-methyl-3-[4-(3-pyridyl)pyrimidin-2-ylamino]phenyl}benzamide This compound was prepared by version of the method described in the document (Synthesis, 1982, 288-291). To 356 mg of 4-methyl-3-[4-(3-pyridyl)pyrimidin-2-ylamino]aniline (Japanese Unexamined Patent Publication (Kokai) No. 6-87834) and 770 mg of 3-bromo-4-(cis-3,5-dimethylpiperazin-1-ylmethyl)benzoic acid dihydrochloride (Reference Example 32), 7 ml of dichloromethane and 715 µl of triethylamine were added in turn. Under stirring at room temperature, 446 mg of phenyl N-phenylphosphoramidochloridate (Synthesis, 1982, 288-291.) was added, following by stirring at room temperature for 2 hours. The reaction solution was mixed with water and then extracted twice with chloroform. The extract was washed with an aqueous saturated sodium hydrogen carbonate solution and dried over anhydrous magnesium sulfate, and then the solvent was distilled off under reduced pressure. The residue was purified in turn by silica gel column chromatography and NH— silica gel column chromatography and the resulting oily product was crystallized from ethyl acetate. The crystal was washed with diethyl ether to obtain 259 mg of the objective compound as a pale yellow crystal.

Melting point: 204-205° C. Elemental analysis (for $C_{30}H_{32}BrN_7O$) Calcd. (%): C, 61.43; H, 5.50; N, 16.72. Found (%): C, 61.19; H, 5.48; N, 16.49

EXAMPLE 35

3-bromo-4-(4-methyl-hexahydro-1H-1,4-diazepin-1-ylmethyl)-N-{4-methyl-3-[4-(3-pyridyl)pyrimidin-2-ylamino]phenyl}benzamide This compound was prepared in the same manner as in Example 34, except that 3-bromo-4-(4-methyl-hexahydro-1H-1,4-diazepin-1-ylmethyl)benzoic acid dihydrochloride (Reference Example 33) was used in place of 3-bromo-4-(cis-3,5-dimethylpiperazin-1-ylmethyl)benzoic acid dihydrochloride.

Pale Yellow Crystal

Melting point: 156-157° C. Elemental analysis (for $C_{30}H_{32}BrN_7O$) Calcd. (%): C, 61.43; H, 5.50; N, 16.72. Found (%): C, 61.13; H, 5.43; N, 16.39

EXAMPLE 36

3-bromo-4-(1-piperazinylmethyl)-N-{4-methyl-3-[4-(5-pyrimidinyl)pyrimidin-2-ylamino]phenyl}benzamide First, 3-bromo-4-[4-(t-butoxycarbonyl)piperazin-1-ylmethyl]-N-{4-methyl-3-[4-(5-pyrimidinyl)pyrimidin-2-ylamino]phenyl}benzamide was prepared by version of the method described in document (Synthesis, 1982, 288-291). In the same manner as in Example 34, except that 4-methyl-3-[4-(5-pyrimidinyl)pyrimidin-2-ylamino]aniline (Reference Example 6) was used in place of 4-methyl-3-[4-(3- pyridyl)pyrimidin-2-ylamino]aniline and 3-bromo-4-[4-(t-butoxycarbonyl)piperazin-1-ylmethyl]benzoic acid (Reference Example 34) was used in place of 3-bromo-4-(cis-3,5-dimethylpiperazin-1-ylmethyl)benzoic acid dihydrochloride, and that extraction was conducted with ethyl acetate and the extract was purified only by silica gel column chromatography and then used for the subsequent reaction without being purified furthermore. Then, 3-bromo-4-(1-piperazinylmethyl)-N-{4-methyl-3-[4-(5-pyrimidinyl)pyrimidin-2-ylamino]phenyl}benzamide was prepared. To 187 mg of the reaction crude product above, 1.5 ml of trifluoroacetic acid was added, followed by stirring at room temperature for 2 hours. The reaction solution was alkalified by adding an aqueous 10% sodium hydroxide solution and dried over anhydrous magnesium sulfate, and then the solvent was distilled off under reduced pressure. The residue was purified by NH-silica gel column chromatography and crystallized by adding ethyl acetate. The crystal was washed with warmed ethyl acetate to obtain 49 mg of the objective compound as a pale yellow crystal.

Pale Yellow Crystal

Melting point: 225-228° C. (with decomposition) Elemental analysis (for $C_{27}H_{27}BrN_8O \cdot 0.3H_2O$) Calcd. (%): C, 57.41; H, 4.92; N, 19.84. Found (%): C, 57.53; H, 5.11; N, 18.92. FAB-MS (Pos.) m/z 559

EXAMPLE 37

4-[4-(t-butoxycarbonyl)piperazin-1-ylmethyl]-3-trifluoromethyl-N-{4-methyl-3-[4-(5-pyrimidinyl)pyrimidin-2-ylamino]phenyl}benzamide This compound was prepared in the same manner as in Example 34, except that 4-methyl-3-[4-(5-pyrimidinyl)pyrimidin-2-ylamino]aniline (Reference Example 6) was used in place of 4-methyl-3-[4-(3-pyridyl)pyrimidin-2-ylamino]aniline and 4-[4-(t-butoxycarbonyl)piperazin-1-ylmethyl]-3-trifluoromethylbenzoic acid (Reference Example 35) was used in place of 3-bromo-4-(cis-3,5-dimethylpiperazin-1-ylmethyl)benzoic acid dihydrochloride, and that extraction was conducted with ethyl acetate and the oily product purified by silica gel column chromatography was crystallized by adding ethanol and then washed in turn with ethanol and diethyl ether.

Pale Yellow Crystal

Melting point: 188-191° C. $^1$H-NMR (CDCl$_3$) δ: 1.47 (9H, s), 2.36 (3H, s), 2.43 (4H, t), 3.45 (4H, t), 3.71 (2H, s), 7.09 (1H, br), 7.18 (1H, d), 7.23 (2H, s), 7.95 (1H, d), 8.05 (2H, d), 8.14 (1H, s), 8.56 (1H, d), 8.65 (1H, br), 9.30 (1H, s), 9.42 (2H, s)

EXAMPLE 38

4-(1-piperazinylmethyl)-3-trifluoromethyl-N-{4-methyl-3-[4-(5-pyrimidinyl)pyrimidin-2-ylamino]phenyl}benzamide To 1.00 g of 4-[4-(t-butoxycarbonyl)piperazin-1-ylmethyl]-3-trifluoromethyl-N-{4-methyl-3-[4-(5-pyrimidinyl)pyrimidin-2-ylamino]phenyl}benzamide (Example 37), 8 ml of trifluoroacetic acid was added, followed by stirring at room temperature for 2 hours. The reaction solution was alkalified by adding an aqueous 10% sodium hydroxide solution and dichloromethane was added. The deposited crystal was collected by filtration to obtain 530 mg of a crude crystal. The filtrate was extracted twice with dichloromethane, dried over anhydrous magnesium sulfate, and then the solvent was distilled off under reduced pressure to obtain 370 mg of a crude crystal. 900 mg of both crude crystals were combined, purified by NH-silica gel column chromatography and then crystallized by adding isopropanol. The crystal was washed in turn with ethyl acetate and diethyl ether to obtain 258 mg of the objective compound as a pale yellow crystal.

Pale Yellow Crystal

Melting point: 208-211° C. Elemental analysis (for $C_{28}H_{27}F_3N_8O$) Calcd. (%): C, 61.31; H, 4.96; N, 20.43. Found (%): C, 61.03; H, 5.01; N, 20.33

EXAMPLE 39

3-methoxycarbonyl-4-(4-methylpiperazin-1-ylmethyl)-N-{4-methyl-3-[4-(3-pyridyl)pyrimidin-2-ylamino]phenyl}benzamide 100 mg of 3-iodo-4-(4-methylpiperazin-1-ylmethyl)-N-{4-methyl-3-[4-(3-pyridyl)pyrimidin-2-ylamino]phenyl}benzamide (Example 2), 1 mg of dichlorobis(triphenylphosphine)palladium(II) and 20 mg of sodium hydrogen carbonate were suspended in 5 ml of anhydrous methanol and the suspension was heated at reflux at a bath temperature of 80° C. for 2 hours while bubbling a carbon monoxide gas into the reaction solution. After air cooling, water and ethyl acetate were added to the reaction solution and insolubles were removed by filtration, and then the filtrate was extracted with ethyl acetate. The extract was washed with water and dried over anhydrous magnesium sulfate, and then the solvent was distilled off under reduced pressure. The residue was purified by silica gel column chromatography and crystallized by adding ethyl acetate-diethyl ether to obtain 64 mg of the objective compound as a colorless crystal.

Melting point: 159-161° C. (with decomposition) Elemental analysis (for $C_{31}H_{33}N_7O_3 \cdot 0.2H_2O$) Calcd. (%): C, 67.06; H, 6.06; N, 17.66. Found (%): C, 66.77; H, 6.03; N, 17.68

EXAMPLE 40

3-cyano-4-(4-methylpiperazin-1-ylmethyl)-N-{4-methyl-3-[4-(3-pyridyl)pyrimidin-2-ylamino]phenyl}benzamide 200 mg of 3-iodo-4-(4-methylpiperazin-1-ylmethyl)-N-{4-methyl-3-[4-(3-pyridyl)pyrimidin-2-ylamino]phenyl}benzamide (Example 2), 35 mg of tetrakis(triphenylphosphine)palladium(0) and 45 mg of 60% zinc cyanide were suspended in 2 ml of anhydrous N,N-dimethylformamide, followed by stirring with heating at 80° C. for 24 hours. After air drying, the reaction solution was mixed with an aqueous saturated sodium hydrogen carbonate solution and extracted twice with chloroform. The extract was dried over anhydrous magnesium sulfate and the solvent was distilled off under reduced pressure. The residue was purified by silica gel column chromatography and crystallized by adding ethanol to obtain 34 mg of the objective compound as a pale yellow crystal.

Melting point: 191-193° C. (with decomposition) Elemental analysis (for $C_{30}H_{30}N_8O \cdot 0.5H_2O$) Calcd. (%): C, 68.29; H, 5.92; N, 21.24. Found (%): C, 68.05; H, 5.99; N, 21.12

EXAMPLE 41

3-bromo-4-(4-methylpiperazin-1-ylmethyl)-N-{4-methyl-3-[4-(5-pyrimidinyl)pyrimidin-2-ylamino]phenyl}benzamide hydrochloride 5.00 g of 3-bromo-4-(4-methylpiperazin-1-ylmethyl)-N-{4-methyl-3-[4-(5-pyrimidinyl)pyrimidin-2-ylamino]phenyl}benzamide (Example 13) was suspended in 250 ml of an aqueous 50% ethanol solution and 9.24 ml of 1N hydrochloric acid was added, followed by stirring with heating in a hot bath at 80° C. to obtain a homogeneous solution. The reaction solution was filtered with heating and the solvent in the filtrate was distilled off under reduced pressure. The residue was dissolved with heating in 30 ml of ethanol and then allowed to stand at room temperature for one day. The deposited crystal was collected by filtration and washed with ethanol to obtain 5.13 g of the objective compound as a pale yellow crystal.

Melting point: 184-186° C. (with decomposition) Elemental analysis (for $C_{28}H_{29}BrN_8O \cdot 1.0HCl \cdot 2.0H_2O$) Calcd. (%): C, 52.06; H, 5.31; N, 17.35. Found (%): C, 51.72; H, 5.17; N, 17.21

EXAMPLE 42

4-(4-methylpiperazin-1-ylmethyl)-3-trifluoromethyl-N-{4-methyl-3-[4-(5-pyrimidinyl)pyrimidin-2-ylamino]phenyl}benzamide hydrochloride This compound was prepared in the same manner as in Example 41, except that 4-(4-methylpiperazin-1-ylmethyl)-3-trifluoromethyl-N-{4-methyl-3-[4-(5-pyrimidinyl)pyrimidin-2-ylamino]phenyl}benzamide (Example 6) was used in place of 3-bromo-4-(4-methylpiperazin-1-ylmethyl)-N-{4-methyl-3-[4-(5-pyrimidinyl)pyrimidin-2-ylamino]phenyl}benzamide.

Pale Yellow Crystal

Melting point: 2.44-246° C. (with decomposition) Elemental analysis (for $C_{29}H_{29}F_3N_8O \cdot 1.0HCl \cdot 0.8H_2O$) Calcd. (%): C, 56.78; H, 5.19; N, 18.27. Found (%): C, 56.80; H, 4.96; N, 18.49

EXAMPLE 43

4-(4-methylpiperazin-1-ylmethyl)-3-trifluoromethyl-N-{3-[4-(5-bromopyridin-3-yl)pyrimidin-2-ylamino]-4-methylphenyl}benzamide hydrochloride This compound was prepared in the same manner as in Example 41, except that 4-(4-methylpiperazin-1-ylmethyl)-3-trifluoromethyl-N-{3-[4-(5-bromopyridin-3-yl)pyrimidin-2-ylamino]-4-methylphenyl}benzamide (Example 10) was used in place of 3-bromo-4-(4-methylpiperazin-1-ylmethyl)-N-{4-methyl-3-[4-(5-pyrimidinyl)pyrimidin-2-ylamino]phenyl}benzamide.

Pale Yellow Crystal

Melting point: 184-187° C. Elemental analysis (for $C_{30}H_{29}BrF_3N_7O \cdot 1.0HCl \cdot 1.0H_2O$) Calcd. (%): C, 51.85; H, 4.64; N, 14.11. Found (%): C, 51.78; H, 4.74; N, 13.92

EXAMPLE 44

4-(4-methylpiperazin-1-ylmethyl)-3-trifluoromethyl-N-{4-methyl-3-[4-(5-pyrimidinyl)pyrimidin-2-ylamino]phenyl}benzamide methanesulfonate 7.00 g of 4-(4-methylpiperazin-1-ylmethyl)-3-trifluoromethyl-N-{4-methyl-3-[4-(5-pyrimidinyl)pyrimidin-2-ylamino]phenyl}benzamide (Example 6) was suspended in 70 ml of methanol and a solution of 1.20 g of methanesulfonic acid in 3 ml of methanol was added dropwise, followed by stirring with heating in an oil bath at 50° C. for 10 minutes. The reaction solution was mixed with 700 mg of activated carbon (Kyoryoku Shirasagi MOIWY433) and then heated at reflux for 30 minutes. The reaction solution was filtered with heating and the solvent in the filtrate was distilled off under reduced pressure. The residue was dissolved with heating in 10 ml of methanol and then allowed to stand at room temperature for 10 minutes. As a result, the entire reaction solution was solidified. The solution was crystallized by adding isopropanol to obtain 7.20 g of the objective compound as a pale yellow crystal.

Melting point: 171-173° C. Elemental analysis (for $C_{29}H_{29}F_3N_8O \cdot 1.0CH_3SO_3H \cdot 1.0H_2O$) Calcd. (%): C, 53.25; H, 5.21; N, 16.56. Found (%): C, 53.04; H, 5.39; N, 16.74

TEST EXAMPLE 1

Cell Growth Inhibitory Effect

K562 cells and U937 cells (purchased from American Type Culture Collection) were cultured in a RPMI-1640 medium (manufactured by Sigma) containing 10% (v/v) fetal calf serum (FCS) (manufactures by Sigma) (RPMI-1640/FCS). K562 cells and U937 cells were seeded at a density of 5000 cells/100 μl/well, respectively. The plate was incubated in a $CO_2$ incubator overnight. A test drug was prepared with dimethylsulfoxide (DMSO) (manufactured by Nacalai Tesque) in the concentration 1000 times higher than the test concentration (0, 0.00001 to 1 μM). The resulting solution was diluted 500 times in a RPMI-1640/FCS medium and then 100 μl of the diluent was added in a well. The plate was incubated in a $CO_2$ incubator. After 72 hours, 20 μl of Cell counting Kit-8 (5 mmol/l WST-8, 0.2 mmol/l 1-Methoxy PMS, 150 mmol/l NaCl) (manufactured by Dojindo) was added to each well. After reaction for color development in a $CO_2$ incubator for 3 hours, an absorbance of formazan, generated by reduction of WST-8 was determined at 450 nm using Multi-level counter ARVOsx (manufactured by Wallac).

$IC_{50}$ value (in μM) was calculated from the following fomula:

cell growth inhibition rate=100−(absorbance of wells with drug/absorbance of wells with 0.1% DMSO)×100

After log-logit transformation, the concentration that gave a cell growth inhibition rate of 50% as defined in $IC_{50}$, was calculated by least square method. The results are shown in Table 1.

As a control drug, 4-(4-methylpiperazin-1-ylmethyl)-N-{4-methyl-3-[4-(3-pyridyl)pyrimidin-2-ylamino]phenyl}benzamide (see Patent Document 1) was used.

TABLE 1

Cell growth inhibitory effect

| Test drugs | K562 cells (IC$_{50}$ value: μM) | U937 cells (IC$_{50}$ value: μM) | Ratio (U937 cells/K562 cells) |
|---|---|---|---|
| Example 1 | 0.0022 | 4.80 | 2181.8 |
| Example 2 | 0.0023 | 3.34 | 1452.2 |
| Example 3 | 0.0046 | 5.01 | 1089.1 |
| Example 4 | 0.033 | 12.40 | 375.8 |
| Example 5 | 0.0008 | 3.99 | 4987.5 |
| Example 6 | 0.0005 | 5.39 | 10780.0 |
| Example 7 | 0.0054 | 6.51 | 1205.6 |
| Example 9 | 0.0017 | 1.86 | 1094.1 |
| Example 10 | 0.0014 | 3.27 | 2335.7 |
| Example 13 | 0.0012 | 6.20 | 5166.7 |
| Example 14 | 0.003 | >10 | >3333.3 |
| Example 15 | 0.0048 | 9.1 | 1895.8 |
| Example 19 | 0.060 | 2.40 | 40.0 |
| Example 20 | 0.015 | 1.82 | 121.3 |
| Example 21 | 0.0053 | >10 | >1886.8 |
| Example 22 | 0.0032 | 6.56 | 2050.0 |
| Example 23 | 0.0094 | >10 | >1063.8 |
| Example 24 | 0.0015 | 7.29 | 4860.0 |
| Example 25 | 0.03 | 17 | 566.7 |
| Example 27 | 0.00049 | 7.16 | 14612.2 |
| Example 28 | 0.00065 | 6.97 | 10723.1 |
| Example 29 | 0.017 | >10 | >588.2 |
| Example 30 | 0.022 | >10 | >454.5 |
| Example 35 | 0.0075 | 5.22 | 696.0 |
| Example 36 | 0.0041 | — | — |
| Example 38 | 0.00093 | — | — |
| Example 39 | 0.035 | >10 | >285.7 |
| Example 40 | 0.0054 | 4.2 | 777.8 |
| control chemical | 0.13 | 17.8 | 136.9 |

As is apparent from the results shown in Table 1, the compounds of the present invention have excellent inhibitory effect for BCR-ABL tyrosine kinase. K562 cells used in Test Example 1 were BCR-ABL positive cells, which had been collected from pleural effusion in a late chronic myelogenous leukemia patient who had been subjected to acute transformation. U937 cells were malignant BCR-ABL negative cells that had been collected from a patient of histiocytic lymphoma. As is apparent from the cell growth inhibitory ratio (U937 cells/K562 cells), the compounds of the present invention are drugs having higher safety than a control drug.

Furthermore, the compounds of the present invention have cell growth inhibitory effect several hundreds times stronger compared to a control drug and therefore it can be expected that they exhibit adequate cell growth inhibitory effect on not only previously known mutant kinases, but also mutant kinases that would be found in the future. Accordingly, the compounds of the present invention are very useful as a therapeutic agent for diseases such as chronic myelogenous leukemia, acute lymphoblastic leukemia and acute myelogenous leukemia.

TEST EXAMPLE 2

Self-phosphorylation Inhibitory Effect on Mutant (E255K) BCR-ABL 293T cells (purchased from ATCC) were cultured in a Dulbecco's Modified Eagle Medium (manufactured by Sigma) containing 10% FCS (DMEM/FCS). The cells were seeded in an amount of 5 ml in a Poly-L-Lysin coated 6 cm dish so as to give $1.2 \times 10^6$ cells/well. The dish was incubated in a $CO_2$ incubator overnight. Using a Lipofectamine reagent (manufactured by Invitrogen), 2 μg of E255K mutant bcr-abl gene expression vector was transfected into the cell. 16 Hours after the transfection 5 μl of a test drug prepared with DMSO (manufactured by Nacalai tesque) so as to give 1000 times higher concentration was added in each well. The dish was incubated in a $CO_2$ incubator for 2 hours. After treatment with trypsin, the cells were collected into a 15 ml centrifuge tube. The tube was centrifuged at 1000 rpm at room temperature for one minute. After removal of the medium, 50 μl of a cell lysis solution was added. The cells were subjected to cytolysis with a mixer. The tube was left to stand at 4° C. for 15 minutes and transferred to 1.5 ml tube. The tube was centrifuged at 12,000 rpm at 4° C. for 15 minutes. The cell lysate was collected into another 1.5 ml tube. The concentration of protein was measured according to BCA method. The samples of cell lysate containing 5 μl of protein was analyzed by SDS-PAGE polyacrylamide. After electrophoresis, the protein was transferred onto a nylon filter (Hybond-P) with wet method at 4° C. overnight. The nylon filter was reacted in 10 ml of PBS/0.1% Tween-20 containing 0.2 μg/ml anti-phosphorylation tyrosin kinase antibody (PY99) (manufactured by Toyobo) at room temperature for one hour. The nylon filter was washed with PBS three times and then reacted 10 ml of PBS/0.1% Tween-20 containing 0.4 μg/ml Anti-mouse IgG AP-conjugated (manufactured by Cell Signaling) at room temperature for one hour. After the nylon filter was washed with PBS four times, self-phosphorylation of p210 BCR-ABL was detected with alkaline phosphatase color developing reagent.

The results are shown as follows: +++: almost perfectly inhibition of phosphorylation; ++: around half of inhibition; +: week inhibition; and –: no inhibition.

As a control drug, 4-(4-methylpiperazin-1-ylmethyl)-N-{4-methyl-3-[4-(3-pyridyl)pyrimidin-2-ylamino]phenyl}benzamide (see Patent document 1) was used.

TABLE 2

Self-phosphorylation inhibitory effect on E255K mutant BCR-ABL

| Test drugs | 0.1 μM | 0.3 μM | 1 μM | 3 μM | 10 μM |
|---|---|---|---|---|---|
| Example 1 | – | – | + | ++ | +++ |
| Example 2 | | + | ++ | +++ | |
| Example 3 | | | – | + | +++ |
| Example 4 | | | – | – | + |
| Example 5 | | | +++ | +++ | +++ |
| Example 6 | – | + | +++ | +++ | +++ |
| Example 7 | | | – | ++ | +++ |
| Example 9 | | | + | ++ | +++ |
| Example 10 | – | – | ++ | +++ | +++ |
| Example 13 | – | + | ++ | +++ | +++ |
| Control chemical | – | – | – | – | – |

As is apparent from the results shown in Table 2, the compounds of the present invention have self-phosphorylation inhibitory effect on E255K mutant BCR-ABL tyrosin kinase. Thus, it is possible to inhibit cell growth caused by the mutant kinase. Particularly, a control drug had no inhibitory effect and therefore it is apparent that this effect is characteristic for the compounds of the present invention.

Furthermore, the compounds of the present invention have also a strong self-phosphorylation inhibitory effect on E255K mutant BCR-ABL tyrosine kinase, on which there is no self-phosphorylation inhibitory effect with some control drugs and therefore it can be expected that they exhibit adequate self-phosphorylation inhibitory effect on mutant kinases that would be found in the future. Accordingly, the compounds of the present invention are very useful as a therapeutic agent for diseases such as chronic myelogenous leukemia, acute lymphoblastic leukemia, acute myelogenous leukemia.

FORMULATION EXAMPLE 1

Tablet (Oral Tablet)

Formulation/tablet (in 80 mg)

| Compound of Example 1 | 5.0 mg |
|---|---|
| Corn Starch | 46.6 mg |
| Crystalline cellulose | 24.0 mg |
| Methyl cellulose | 4.0 mg |
| Magnesium stearate | 0.4 mg |

The mixed powder of this composition is compressed by a conventional method and molded to make oral tablets.

FORMULATION EXAMPLE 2

Tablet (Oral Tablet)

Formulation/tablet (in 80 mg)

| Compound of Example 2 | 5.0 mg |
|---|---|
| Corn Starch | 46.6 mg |
| Crystalline cellulose | 24.0 mg |
| Methyl cellulose | 4.0 mg |
| Magnesium stearate | 0.4 mg |

The mixed powder of this composition is compressed by a conventional method and molded to make oral tablets.

INDUSTRIAL APPLICABILITY

As described above, since the compound of the present invention is a compound having excellent BCR-ABL tyrosine kinase inhibitory activity, a pharmaceutical composition comprising the compound of the present invention as an active ingredient is useful as a BCR-ABL tyrosine kinase inhibitor, a therapeutic agent for chronic myelogenous leukemia, a therapeutic agent for acute myelogenous leukemia and a therapeutic agent for acute lymphoblastic leukemia for mammals including humans.

The invention claimed is:

1. An amide derivative represented by the following formula [1], or a salt thereof;

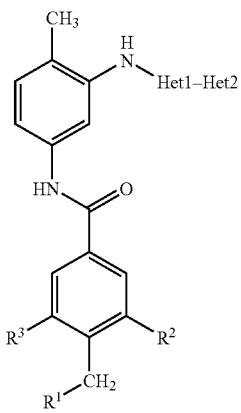

$R^1$ represents a saturated cyclic amino group (the saturated cyclic amino group may be substituted by 1 to 3 same or different members selected from the group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl), monoalkylamino or dialkylamino;

$R^2$ represents alkyl, halogen, haloalkyl, hydroxyalkyl, alkoxy, alkoxyalkyl, alkoxycarbonyl, acyl, amino, monoalkylarmino, dialkylamino, nitro, carbamoyl, monoalkylcarbamoyl, dialkylcarbamoyl or cyano;

$R^3$ represents hydrogen, halogen or alkoxy;

Het1 represents any of groups of the following formulas [2] to [8];

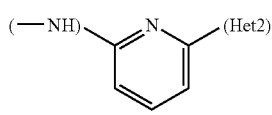

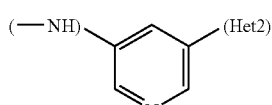

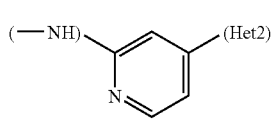

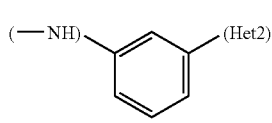

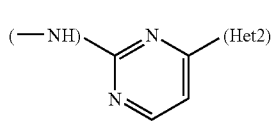

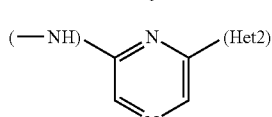

-continued

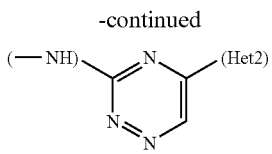

[8]

Het2 represents pyridyl, pyrimidinyl, pyrazinyl, pyridazinyl or 1, 2-dihydropyridazinyl (the Het2 may be substituted by 1 to 3 same or different members selected from the group consisting of alkyl, halogen and amino);

Excluding compound wherein $R^1$ is (i) pyrrolidinyl, piperidinyl, piperazinyl or morpholinyl, all of which may be substituted by 1 to 3 same or different members selected from the group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl, (ii) monoalkylamino, or (iii) dialkylamino, Het1 is a group of the formula [6], and Het2 is pyrazinyl or pyridyl which may be substituted by alkyl.

2. The amide derivative according to claim 1, or a salt thereof, wherein $R^1$ is a saturated cyclic amino group (the saturated cyclic amino group may be substituted by 1 to 3 same or different members selected from the group consisting of alkyl and alkoxycarbonyl), monoalkylamino or dialkylamino, $R^2$ is alkyl, halogen, haloalkyl, alkoxy, alkoxycarbonyl, nitro, dialkylcarbamoyl or cyano, $R^2$ is hydrogen, halogen or alkoxy, Het1 is any of groups of the formulas [2] to [8], and Het2 is pyridyl, pyrimidinyl, pyrazinyl, pyridazinyl or 1,2-dihydropyridazinyl (the Het2 may be substituted by 1 to 3 same or different halogen).

3. The amide derivative according to claim 1, which is a compound selected from the group consisting of the following compounds (1) to (18), or a salt thereof:

(1) 4-(4-methylpiperazin-1-ylmethyl)-3 -trifluoromethyl-N-{4-methyl-3-[4-(5-pyrimidinyl)pyrimidin-2-ylamino]phenyl}benzamide, (2) 3-bromo-4-(4-methylpiperazin-1-ylmethyl)-N-{3-[4-(6-chloropyridin-3-yl)pyrimidin-2-ylamino]-4-methylphenyl}benzamide, (3) 3-bromo-4-(4-methylpiperazin-1-ylmethyl)-N-{3-[4-(5-bromopyridin-3-yl)pyrimidin-2-ylamino]-4-methylphenyl}benzamide, (4) 4-(4-methylpiperazin-1-ylmethyl)-3-trifluoromethyl-N-{3-[4-(5-bromopyridin-3-yl)pyrimidin-2-ylamino]-4-methylphenyl}benzamide, (5) 3-bromo-4-(4-methylpiperazin-1-ylmethyl)-N-{3-[4-(1,2-dihydropyridazin-4-yl) pyrimidin-2-ylamino]-4-methylphenyl}benzamide, (6) 3-bromo-4-(4-methylpiperazin-1-ylmethyl)-N-{4-methyl-3-[4-(3-pyridazinyl)pyrimidin-2-ylamino]phenyl}benzamide, (7) 3-bromo-4-(4-methylpiperazin-1-ylmethyl)-N-{4-methyl-3-[4-(5-pyrimidinyl)pyrimidin-2-ylamino]phenyl}benzamide, (8) 3-bromo-4-(4-methylpiperazin-1-ylmethyl)-N-{4-methyl-3-[4-(3-pyridyl)pyridin-2-ylamino]phenyl}benzamide, (9) 3-bromo-4-(4-methylpiperazin-1-ylmethyl)-N-{4-methyl-3-[4-(5-pyrimidinyl)pyridin-2-ylamino]phenyl}benzamide,

(10) 3-bromo-4-(4-methylpiperazin-1-ylmethyl)-N-{4-methyl-3-[2-(3-pyridyl)pyridin-6-ylamino]phenyl}benzamide,

(11) 3-bromo-4-(4-methylpiperazin-1-ylmethyl)-N-{4-methyl-3-[3-(3-pyridyl)pyridin-5-ylamino]phenyl}benzamide,

(12) 3-bromo-4-(4-methylpiperazin-1-ylmethyl)-N-{4-methyl-3-[3-(3-pyridyl)phenylamino]phenyl}benzamide,

(13) 3-bromo-4-(4-methylpiperazin-1-ylmethyl)-N-{4-methyl-3-[2-(3-pyridyl)pyrazin-6-ylamino]phenyl}benzamide,

(14) 3-bromo-4-(4-methylpiperazin-1-ylmethyl)-N-{4-methyl-3-[5-(3-pyridyl)-1,2,4-triazin-3-ylamino]phenyl}benzamide,

(15) 3-bromo-4-(4-methyl-hexahydro-1H-1,4-diazepin-1-ylmethyl)-N-{4-methyl-3-[4-(3-pyridyl) pyrimidin-2-ylamino]phenyl}benzamide,

(16) 3-bromo-4-(1-piperazinylmethyl)-N-{4-methyl-3-[4-(5-pyrimidinyl)pyrimidin-2-ylamino]phenyl}benzamide,

(17) 4-[4-(t-butoxycarbonyl)piperazin-1-ylmethyl]-3-trifluoromethyl-N-{4-methyl-3-[4-(5-pyrimidinyl) pyrimidin-2-ylamino]phenyl}benzamide, and

(18) 4-(1-piperazinylmethyl)-3-trifluoromethyl-N-{4-methyl-3-[4-(5-pyrimidinyl)pyrimidin-2-ylamino)phenyl}benzamide.

4. A pharmaceutical composition comprising the amide derivative of claim 1 or a salt thereof as an active ingredient and a pharmaceutically acceptable carrier.

5. A method of treating a subject having acute lymphoblastic leukemia comprising administering to the subject an effective amount of the amide derivative of claim 1 or a salt thereof.

6. A method of treating a subject having acute myelogenous leukemia comprising administering to the subject an effective amount of the amide derivative of claim 1 or a salt thereof.

7. A method of treating a subject having acute myelogenous leukemia comprising administering to the subject an effective amount of the amide derivative of claim 1 or a salt thereof.

* * * * *